(12) United States Patent
Kumar et al.

(10) Patent No.: US 6,727,097 B2
(45) Date of Patent: Apr. 27, 2004

(54) METHOD AND APPARATUS FOR ACCELERATED CATALYST POISONING AND DEACTIVATION

(75) Inventors: Sanath V. Kumar, North Brunswick, NJ (US); James Rogalo, Rockaway, NJ (US)

(73) Assignee: Engelhard Corporation, Iselin, NJ (US)

( * ) Notice: Subject to any disclaimer, the term of this patent is extended or adjusted under 35 U.S.C. 154(b) by 55 days.

(21) Appl. No.: 09/803,606

(22) Filed: Mar. 9, 2001

(65) Prior Publication Data

US 2002/0022272 A1 Feb. 21, 2002

Related U.S. Application Data

(63) Continuation-in-part of application No. 09/594,399, filed on Jun. 15, 2001, now Pat. No. 6,586,254.

(51) Int. Cl.⁷ .............................................. G01N 31/10
(52) U.S. Cl. .................... 436/37; 436/155; 436/159
(58) Field of Search ................ 436/37, 155, 159, 436/181, 183

(56) References Cited

U.S. PATENT DOCUMENTS

| | | | |
|---|---|---|---|
| 3,904,551 A | 9/1975 | Lundsager, et al. | 252/455 |
| 4,329,162 A | 5/1982 | Pitcher, Jr. | 55/523 |
| 4,340,403 A | 7/1982 | Higuchi et al. | 55/523 |
| 4,364,760 A | 12/1982 | Higuchi et al. | 55/523 |
| 4,403,008 A | 9/1983 | Factor | 428/117 |
| 4,510,265 A | 4/1985 | Hartwig | 502/330 |
| 4,519,820 A | 5/1985 | Oyobe et al. | 55/284 |
| 4,559,193 A | 12/1985 | Ogawa et al. | 264/60 |
| 4,563,414 A | 1/1986 | Ogawa et al. | 430/325 |
| 4,674,447 A | 6/1987 | Davis | 123/1 A |
| 4,714,694 A | 12/1987 | Wan et al. | 502/304 |
| 4,727,746 A | 3/1988 | Mikasa et al. | 73/23 |
| 4,771,029 A | 9/1988 | Pereira et al. | 502/355 |
| 5,057,483 A | 10/1991 | Wan | 502/304 |
| 5,100,632 A | 3/1992 | Dettling et al. | 423/213.5 |
| 5,696,065 A | 12/1997 | Tanaka et al. | 508/465 |

FOREIGN PATENT DOCUMENTS

| | | | |
|---|---|---|---|
| EP | 0 719 851 B1 | 2/2000 | C10M/135/18 |
| JP | 55-79046 | * 6/1980 | |
| WO | WO 92/09848 | 6/1992 | F23D/14/00 |
| WO | WO 95/00235 | 1/1995 | B01D/53/36 |
| WO | WO 95/35152 | 12/1995 | B01D/53/94 |
| WO | WO 96/17671 | 6/1996 | B01D/53/94 |
| WO | WO 99/55459 | 11/1999 | B01J/37/02 |

OTHER PUBLICATIONS

Kim, G. et al, Industrial & Engineering Chemistry Product Research and Development 1984, 23, 525–531.*
Williamson, W.B. et al, Applied Catalysis 1985, 15, 277–292.*
Tabata, T. et al, Applied Catalysis B 1995, 7, 19–32.*
Angelidis, T. N. et al, Applied Catalysis A 1995, 133, 121–132.*
SAE 790943, "The Influence of Sulfur Species on the Laboratory Performance of Automotive Three Component Control Catalysts", Joy, Lester and Molinaro, Oct. 1–4, 1979.

(List continued on next page.)

*Primary Examiner*—Arlen Soderquist
(74) *Attorney, Agent, or Firm*—Richard A. Negin

(57) ABSTRACT

An article, apparatus and method for simulating poisoning and deactivating catalysts with catalyst poison compounds at least one catalyst poison compound selected from the group consisting of a compound comprising phosphorous, a compound comprising zinc compound and a compound comprising phosphorous and zinc.

16 Claims, 15 Drawing Sheets

OTHER PUBLICATIONS

SAE 821193, "Effects of Fuel Additive MMT on Contaminant Retention and Catalyst Performance", Williamson, Gandhi and Weaver, Oct. 18–21, 1982.

SAE 860298, "Update on the Evaluation of Diesel Particulate Filters for Underground Mining", Lawson, Vergeer, Stawsky, Daniel and Thimons, Feb. 24–28, 1986.

SAE 892040, "High Temperature Deactivation of Three-Way Catalyst", Carol, Newman and Mann, Sep. 25–28, 1989.

SAE 930937, "Deterioration of Three-Way Automotive Catalysts, Part 1—Steady State and Transient Emission of Aged Catalyst", Jobson, Laurell, Högberg, Bernier, Lundgren, Wirmark and Smedler, Mar. 1–5, 1993.

SAE 940746, "Engine Oil Additive Effects on Deactivation of Monolithic Three-Way Catalysts and Oxygen Sensors", Ueda, Sugiyama, Arimura, Hamaguchi and Akiyama, Feb. 28–Mar. 3, 1994.

SAE 950934, "Computer Aided Assessment of Catalyst Aging Cycles", Pattas, Stamatelos, Koltsakis and Konstantinidis, Feb. 27–Mar. 2, 1995.

SAE 972,842, "Impact of Oil–Derived Catalyst Poisons on FTP Performance of LEV Catalyst Systems", Beck, Sommers, DiMaggio and Monroe, Oct. 13–16, 1997.

SAE 972846, "Application of Accelerated Rapid Aging Test (RAT) Schedules with Poisons: The Effects of Oil Derived Poisons, Thermal Degradation and Catalyst Volume on FTP Emmissions", Ball, Mohammed and Schmidt, Oct. 13–16, 1997.

SAE 2000–01–0214, "Numerical Simulation of Deactivation Process of Three-Way Catalytic Converters", Baba, Yokota, Matsunaga, Kojima, Ohsawa, Ito and Domyo, pp. 117–131.

"Three-Way Catalyst Deactivation by Lubricants During Fast Aging Engine Test", Natoli, Pometto, Salino and Guerzoni, Gionale ed Atti della Associazione Technica dell'Automobile, vol. 48, No. 12, p. 685, Dec. 1995.

* cited by examiner

Laboratory Zn/P Doped Catalyst P Profile    Engine Aged Catalyst P Profile

× Reference 1050C Aged    ○ Zn/P-Doped 1050C Aged    - P-Doped 1050C Aged

■ HC% 2340AL2
△ HC% 2341AL2

■ HC% 2340BL2
△ HC% 2341BL2

■ HC% 2340CL2
△ HC% 2341CL2

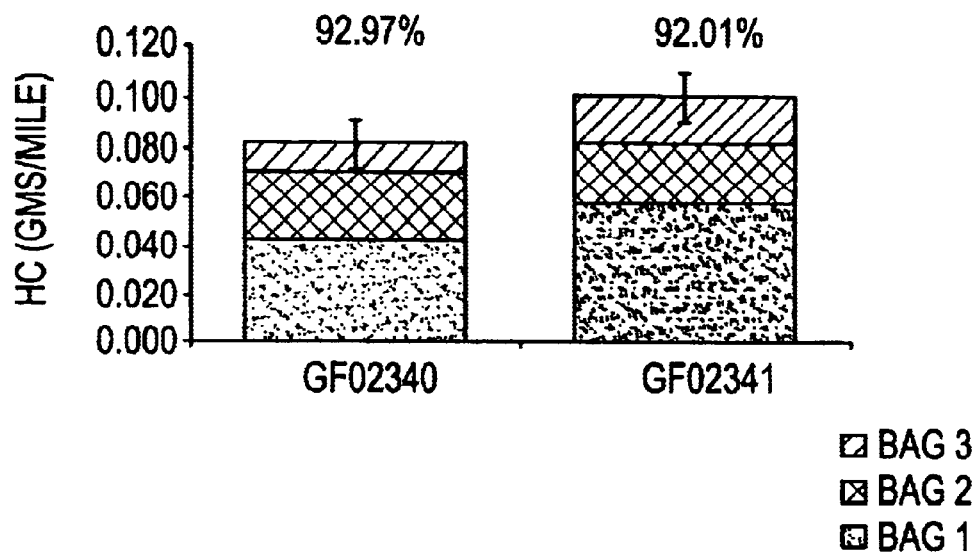
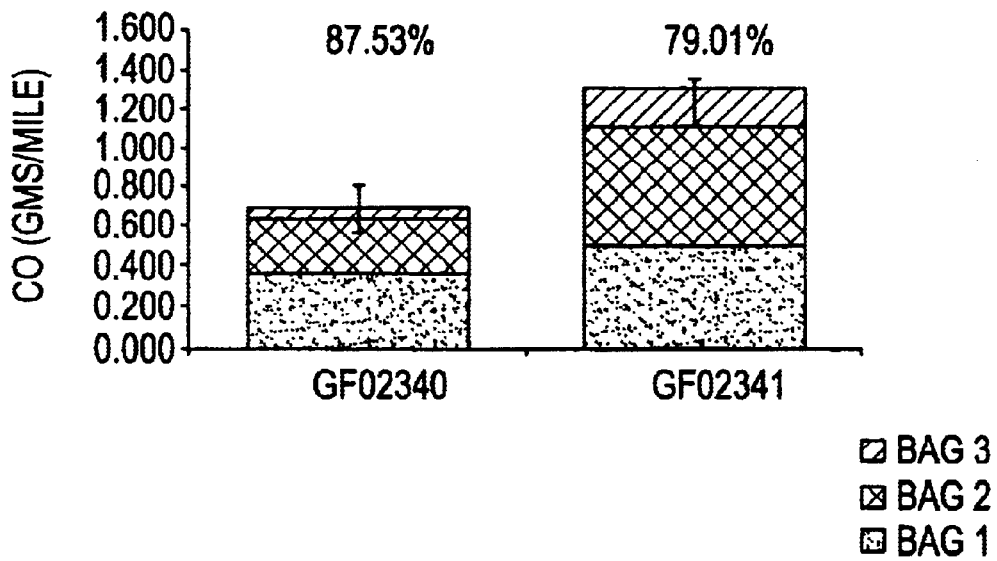

P Profile with Oil Injection

P Profile without Oil Injection

METHOD AND APPARATUS FOR ACCELERATED CATALYST POISONING AND DEACTIVATION

CROSS REFERENCE TO RELATED APPLICATION

This application is a continuation-in-part of application Ser. No. 09/594,399 filed Jun. 15, 2001, now U.S. Pat. No. 6,586,254.

BACKGROUND OF THE INVENTION

1. Field of the Invention

The present invention relates to a method and apparatus useful for evaluation of catalysts. More particularly, the present invention is directed to simulating poisoning and deactivating catalysts with catalyst poison compounds at least one catalyst poison compound selected from the group consisting of a compound comprising phosphorous, a compound comprising zinc compound and a compound comprising phosphorous and zinc.

2. Description of the Related Art

The art discloses that additives such as lubricants used in internal combustion engine oils can contain compounds which contain phosphorous and/or zinc. Such compounds include materials such as zinc dialkyldithiophosphate also referred to as zinc dithiophosphate (ZDTP) and zinc dithiocarbamate (ZDTC). Other disclosed zinc and phosphorous additives to oil include metallic detergents including phosphorares and phosphorous compounds included as extreme pressure agents. Reference is made to U.S. Pat. Nos. 4,674,447 and 5,696,065 and European Application No. 95309415. The phosphorous and zinc are disclosed to lower the function of the motor vehicle exhaust treatment catalyst.

As engine technology and exhaust gas treatment technology has improved engines pass less lubricating oil, including phosphorous and zinc compound to the catalysts and the catalysts have been sufficiently active to treat exhaust gases in accordance with various government regulations. However, as engine performance continues to increase and environmental regulations become more stringent catalysts activity will have to be increased and maintained with longer engine life. As engine life increases there will be a greater build up of compounds, particularly phosphorous and/or zinc compounds passing to the emission treatment catalyst from the engine. It is desirable to have a method to simulate the poisoning of the catalyst poisoning and deactivation in the laboratory for different engine systems run at different conditions to for various reasons including to more rapidly screen new catalysts.

Numerous methods have been used in the past to simulate long term deactivation of a catalyst, using an engine bench test. Most of these methods involve running an engine at very high speed and load conditions cyclically for several hours, often creating a large exotherm in the catalyst bed during certain portions of the test cycle. These adverse conditions deactivate the catalytic converter, and a correlation is drawn between this type of rapid aging cycle and on-road deactivation of the emission control system in general, and catalytic converter, in particular. While such correlations can be developed, they do not always mimic the actual deactivation modes, such as poison accumulation.

References such as U.S. Pat. No. 4,771,029 disclose the ad recognition of catalyst poisoning by materials such as phosphorous. U.S. Pat. No. 4,727,746 discloses a modal mass analysis method for simulating driving conditions for evaluating exhaust gases.

Ueda et al., *Engine Oil Additive Effects on Deactivation of Monolithic Three-Way Catalysts and Oxygen Sensors*, SAE, SP-1043, 1994, discloses that it is widely known that ZDTP results in phosphorous poisoning of three-way emissions catalysts. Catalysts and oxygen sensors were "poisoned" on the engine bench by test oils, varying the quantity of phosphorous and ash. The performance of the catalysts and sensors was evaluated using a FTP test on a chassis dynamometer. It was found that calcium and magnesium helped prevent the phosphorous from adhering to the catalyst.

Joy et al., *The Influence of Sulfur Species on the Laboratory Performance of Automotive Three Component Control Catalysts*, SAE, 1979, discloses that poisons such as phosphorous and sulfur poison catalysts. Studies were done in the laboratory on the effects of sulfur dioxide.

Baba et al., *Numerical Simulation of Deactivation Process of Three-way Catalytic Converters*, SAE, SP-1533, Mar. 6, 2000, discloses a numerical simulation method to predict the deactivation process of three-way catalytic converters. Based on simulated results of the deactivated state inside the bench aged catalysts, which are noble metal particle size and catalyst activity distributions, thermal responses and light-off behaviors during warm-up tests are predicted.

Natoli et al., *Three-way Catalyst Deactivation by Lubricants During Fast Aging Engine Tests*, Gionale ed Atti della Associazione Technica dell'Automobile, Vol. 48, No. 12, p 685, 1995 discloses that engine lubricants play an important role in poisoning three-way catalytic converters. The objective was to reproduce in the laboratory the aging of the catalysts under accelerated conditions in order to evaluate the influence of additive contained in engine oils.

Ball et al., *Application of accelerated Rapid Aging Test (RAT) Schedules with Poison: The Effects of Oil Derived Poisons, Thermal Degradation and catalyst Volume on FTP Emissions*, SAE, SP-1296, 43-53, 1997 discloses dynamometer rapid aging tests incorporate both thermal and oil-derived poison degradation are used to age catalysts for FTP emissions studies. Vehicle aged converters are analyzed to determine the axial aged phosphorous distribution throughout the catalyst. These profiles are compared to dynamometer aged RAT aged catalysts.

Other references of interest include: Carol et al., *High temperature Deactivation of Three-way Catalyst*, SAE, 1989; Pattas et al., *Computer Aided Assessment of Catalyst Aging Cycles*, SAE, 1995. Beck et al., *Impact of Oil-derived Catalyst Poisons on FTP Performance of LEV Catalyst Systems*, SAE, SP-1296, 1–10, 1997. Jobson et al., *Deterioration of Three-way Automotive Catalysts*, SAE, SP-957, 153–66, 1993; and Williamson et al., *Effects of Oil Phosphorous on Deactivation of Monolithic Three-way Catalysts*, Appl. Catal. (1985), 15(2), 277–92.

SUMMARY OF THE INVENTION

Automotive catalytic converters and filters comprise at least one catalyst composition. Such catalyst compositions are susceptible to poisoning due to lubricant oil—derived phosphorus, zinc, sulfur and other compounds. Catalyst compositions (referred to as "catalysts") can be coated on to a suitable substrate. The coated catalyst when applied to the substrate in a slurry or liquid form is also referred to as a "washcoat". The poisons may accumulate on the surface of the washcoat, creating a physical barrier, or they may interact with the catalytic material in the washcoat, resulting in loss of catalytic activity, and/or become a barrier to particulate filters such as foam, screens and wallflow filters.

The poison level and type can vary, depending upon the design of the engine and the operating conditions. In the development of the emission control system, it is critical to know the type of poison a exposure and the impact of poison on the emissions control system in general, and the catalytic converter, in particular.

The present invention relates to a method and apparatus that effectively duplicates these poisoning conditions in a laboratory environment. In addition, the invention relates to a method and apparatus that duplicates, on an engine test stand, the equivalent of extended on road-type poison exposure, deposition and catalyst deactivation and/or filter clogging.

It is generally known that lubricant-derived phosphorus, zinc and sulfur can accumulate on the catalyst surface and result in deactivation. This poisoning mechanism is quite complex, and highly dependent upon the operating temperature, the oil consumption of the engine, and the source of the oil consumption. For example, when oil leaks past the piston rings, and washes into the combustion chamber, it goes through the combustion process. This will result in certain types of phosphorus and/or zinc compounds (among other contaminants). Particular compounds may have a certain type of deactivation effect on the catalytic converter, depending upon the operating condition. On the other hand, oil that leaks past the exhaust valve guide and stem, may not go through the combustion process, and result in a different type of poisoning of the catalytic converter.

Numerous methods have been used in the past to simulate long term deactivation of a catalyst, using an engine bench test. Most of these methods involve running an engine at very high speed and load conditions cyclically for several hours, often creating a large exotherm in the catalyst bed during certain portions of the test cycle. These adverse conditions deactivate the catalytic converter, and a correlation is drawn between this type of rapid aging cycle and on-road deactivation of the emission control system in general, and catalytic converter, in particular. While such correlations can be developed, they do not always mimic the actual deactivation modes, such as poison accumulation. In this invention, a method has been developed to accelerate the catalyst aging process, with poison deposition on an emission treatment device which are typically a catalyst and/or a filter. The catalyst can be a catalyst composition in self supported form such as a powder, pellet or other form article, or in a supported form wherein the catalyst composition is supported on a suitable substrate such as a monolithic article which can be a metallic or ceramic flow through or wall flow honeycomb, wire mesh and ceramic foam.

In accordance with the method of the present invention, an emission treatment device selected from at least one of a catalyst and a filter, is combined with at least one poison compound having at least one component selected from the group consisting phosphorous, zinc and sulfur to form a poisoned emission treatment device.

The poisoned emission treatment device is heated at suitable temperatures, typically from about 200° C. to about 1100° C., preferably from about 300° C. to about 800° C., more preferably from about 300° C. to about 500° C., most preferable about 400° C. for a sufficient time to calcine poisoned device. Typically the calcination time is from about 0.5 hours to about 24 hours preferably from about 1.0 hours to about 12 hours, more preferably from about 2.0 hours to about 8.0 hours, most preferable from about 3.0 hours to about 6.0 hours to form a calcined emission treatment device. The activity of the calcined emission treatment device can then be evaluated. The evaluation can include evaluating catalytic activity of an exhaust treatment catalyst to determine the conversion percent of at least one pollutant component by the catalyst, the light-off temperature of at least one pollutant component at a catalyst, and/or the efficiency of a filter.

In a specific embodiment, accordance with the method of the present invention the emission treatment device can be combined with poisons provided by a the operation of a gasoline or diesel engine, having an exhaust gas outlet or an exhaust gas manifold outlet. The engine can be on a bench stand in the laboratory or on a motor vehicle. An exhaust gas stream comprising pollutants selected at least one pollutant component selected from the group consisting of carbon monoxide, hydrocarbons and nitrogen oxides, volatile organic components and dry soot, from the exhaust gas outlet or the exhaust gas manifold outlet of the engine is passed to the emission treatment device. At least one poison compound having at least one component selected from the group consisting phosphorous, zinc and sulfur can be added to the exhaust gas stream at a location between the exhaust gas outlet or the exhaust gas manifold outlet and the emission treatment device. The exhaust gas containing the poison compound can then contact the emission treatment device to form a poisoned emission treatment device. The emission treatment device can then be evaluated.

In another specific embodiment the gasoline or diesel engine have an oil pan in which lubricating oil is located. At least one poison compound having at least one component selected from the group consisting phosphorous, zinc and sulfur is added to the oil in an amount in excess of the amount functionally required for the oil to function. The emission treatment device can then be evaluated.

In an alternative and preferred embodiment, the emission treatment device can be combined with at least one poison compound or precursor compound having at least one component selected from the group consisting phosphorous, zinc and sulfur. The poison or poison precursor can be applied directly to the emission treatment device. The device can then be calcined. Where the device is a filter or catalyzed substrate the poison or poison precursor can be coated with a solution or slurry, sprayed, or deposited by other suitable methods. The poisoned device can then be evaluated. In preferred embodiments, catalyzed substrates are coated with a slurry containing the poison or poison precursor. The coated substrate can be calcined, if necessary, and then evaluated. This provided a rapid way to screen the effect of poisons on various catalyst compositions. The method is particularly useful to evaluate the catalysts useful as gaseous emissions exhaust catalyst. Such catalysts typically are used to treat at least one pollutant component selected from the group consisting of carbon monoxide, hydrocarbons and nitrogen oxides, volatile organic components and dry soot.

In an alternative embodiment the emission treatment device (e.g., the catalyst) to be aged is mounted on an engine test bench. The lubricating oil in the engine may be doped with high levels of catalyst poison or poison precursor such as zinc dialkyl dithiophosphate (ZDDP), a commercially available phosphorus/Zinc/Sulfur compound. Alternatively or in combination, an apparatus can be set up to inject ZDDP-containing engine oil directly into the exhaust stream, ahead of the catalytic converter. The level of ZDDP and the amount of oil injected can be varied, depending upon the degree of deactivation required. The engine can then run through a combination of high speed and load (to thermally deactivate the catalyst), and low speed/low load conditions combined with injection of the oil into the exhaust stream (to deposit the poisons on the catalytic surface). This combination of high and low temperature operation is run cyclically or sequentially, until the desired level of deactivation is achieved. In general, exhaust gas temperatures during accelerated aging on an engine dynamometer or a laboratory reactor can be vary, from about 300° C. during low load and low speed operation, and up to about 1200° C. during high load and high speed operation. More specifically, the exhaust gas temperatures can be vary, in the range of 300° C. to 1200° C. Alternatively, operating ranges can be from about 300° C. to about 600° C. during low speed and low load operation, or from about 600° C. to about 1200° C. during high speed and high load operation.

The present invention includes a method of introducing the poison-containing oil into the exhaust stream at the above conditions. The process of introducing engine lubricating oil (with or without elevated levels of poisonous compounds) is critical. For instance, if oil is dripped or injected into the exhaust stream, it could coke or oxidize at the point of introduction, and may 1) never reach the catalyst washcoat surface, or 2) coke and block the nozzle or other device used to drip or inject the oil into the exhaust stream.

In accordance with the method of the present invention, coking of oil in the process of accelerated aging of a catalytic converter on an engine dynamometer or a laboratory reactor is prevented or minimized. Forcing the oil in to the exhaust stream as a mist with the assistance of high pressure nitrogen or other inert gas is one embodiment of the present invention. This assists in keeping the flow nozzle clear during certain types of catalyst aging.

Another embodiment of this invention is the introduction of both high pressure nitrogen (or other inert gas) and water with the oil. The oil, water and nitrogen have to be introduced at predetermined rates and pressures, sufficient to keep a clear flow through the injection nozzle or orifice. This method results in the emulsification of the oil by the water. As the mixture comes in contact with the hot walls of the injector and tube, some coking will begin. However, the water in the emulsion evaporates at these temperatures, and thus cleans out the oil flow passage. This self-cleaning mechanism is preferred to keeping a continuous flow of oil into the exhaust gas stream for the entire duration of oil injection during certain arduous the accelerated aging test protocol.

The method and apparatus of the present invention are particularly useful when the emission treatment device comprises a catalyst supported on a substrate. In preferred embodiments the catalyst comprises a catalyst composition comprising a support; and at least one catalytic material selected from the group consisting of at least one platinum group metal component, gold and silver. The platinum group metal component can be selected from at least on component selected from the group consisting of platinum, palladium, rhodium, ruthenium and iridium.

The method is useful to evaluate the effect of poisons selected from the group of a compound comprising phosphorous, a compound comprising zinc compound, a sulfur compound, a compound comprising phosphorous and zinc, a compound comprising zinc and sulfur and a compound comprising phosphorous zinc and sulfur. Typically, the compounds comprising phosphorous are selected from the group consisting of ammonium hydrophosphate, phosphoric acid, phosphorus acid, and organo phosphorus compounds; compounds comprising zinc is selected from the group consisting of zinc oxide, zinc nitrate, zinc sulfate, zinc carbonate and organo zinc compounds; and the compound mixtures comprising phosphorous, and zinc can be selected from the group consisting of a mixture of zinc oxide and ammonium hydrophosphate, zinc dithio phosphate, and zinc phosphate.

Where the poison is added to the lubricating oil, it will be in excess of the amount typically in lubricating oil. The amount of poison or poison precursor is typically greater than about 0.15 weight percent of the oil and poison or poison precursor, and preferably from about 0.15 to 0.5, more preferably from 0.2 to 0.5 poison or poison precursor.

In a preferred method the compound mixture comprising phosphorous and zinc and optionally sulfur compounds is a in a slurry. A preferred mixture is an aqueous slurry of zinc oxide and ammonium hydrophosphate. The slurry is then coat applied, typically by coating or spraying on to a catalyst which is preferably a catalyst composition located on a substrate, on to a filter such as a wall flow filter. As necessary, and preferably the poisoned is calcined.

In typical evaluations the amount of the catalyst poison compound is from about 1.0 to about 20 weight percent of the catalyst.

The step of evaluating the catalytic activity of the gaseous emissions exhaust catalyst comprises contacting a synthetic gas comprising at least one pollutant component with the poisoned catalyst at predetermined conditions of temperature, time and pollutant component concentration to determine the conversion percent of at least one pollutant component and/or the light-off temperature of at least one pollutant component. The catalyst can have poison added at a predetermined rate. Catalyst light off is the temperature at which 50% conversion of a given pollutant is converted. This can be determined using flame ionization detector to measure hydrocarbon conversion. Carbon monoxide conversion can be measured using nondispersive infrared (NDIR) analysis. Nitrogen oxide conversion can be determined using a chemiluminescence analyzer.

Pressure drop, weight game, micro photographs can be used to assess the effect of poison as becoming a barrier to a filter.

The present invention further includes as an article, an emission treatment device selected from at least one of a catalyst and a filter. The emission treatment device has an over coat of a predetermined amount at least one poison or poison precursor compound having at least one component selected from the group consisting phosphorous, zinc and sulfur.

Where the article comprises an exhaust treatment catalyst. The catalyst comprises a composition having a support and at least one platinum group metal component selected from the group consisting of platinum, rhodium, ruthenium and iridium components.

In a specific embodiment the article comprises a catalyst supported on a substrate having channel extending from an inlet end to an outlet end and the poison is deposited in varying concentrations from the inlet to the outlet. The poison can be deposited in zones having different concentrations from the inlet to the outlet. The poison can be deposited in an inlet zone having a higher concentrations then an outlet zone located between the inlet zone and the outlet end.

The present application further includes an apparatus comprising a gasoline or diesel engine, having an exhaust gas outlet or an exhaust gas manifold outlet. There is an emission treatment device selected from at least one of a catalyst and a filter. A conduit communicates between the exhaust gas outlet or an exhaust gas manifold outlet and the emission treatment device. An overcoat on the catalyst composition has a predetermined amount of at least one poison compound or poison precursor having at least one component selected from the group consisting phosphorous, zinc and sulfur. There is feed port into the conduit at a location between the exhaust gas outlet or the exhaust gas manifold outlet and the emission treatment device; and a means to feed through the feed port at least one poison or a compound capable of forming the poison and having at least one component selected from the group consisting phosphorous, zinc and sulfur. There is a means to evaluate the emission treatment device to determine the conversion percent of at least one pollutant component by the catalyst, the light-off temperature of at least one pollutant component at the catalyst, and/or the efficiency of the filter.

BRIEF DESCRIPTION OF DRAWINGS

FIG. 10 is a graph showing FTP tailpipe HC emissions for catalysts aged with and without oil injection in Example 5.

FIG. 11 is a graph showing FTP tailpipe Co emissions for catalysts aged with and without oil injection in Example 5.

DETAILED DESCRIPTION OF THE PREFERRED EMBODIMENTS

The present invention will be understood by those skilled in the art by reference to following description of the preferred embodiments including the examples, and the accompanying drawings.

This invention, relates to an apparatus and method to accelerate the catalyst aging process, with poison deposition on an emission treatment device which are typically a catalyst and/or a filter.

Figure 1:
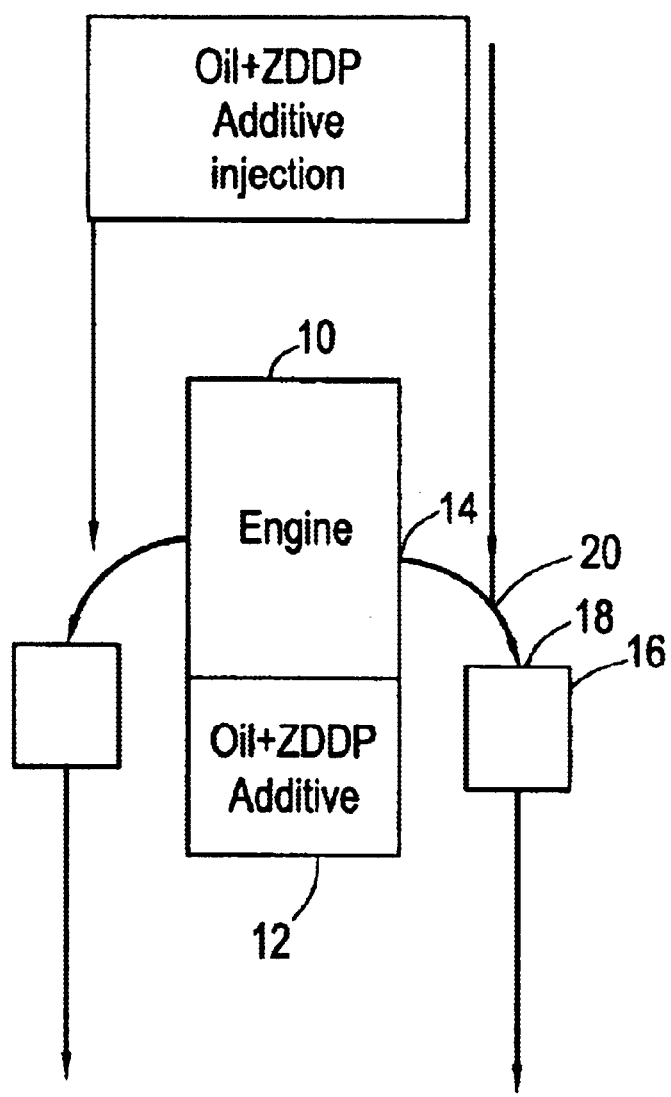
FIG. 1 is a general schematic diagram of catalyst aging system of the present invention.

FIG. 1 is a schematic drawing of an apparatus of the present invention. In this embodiment there is an engine 10 in communication with an oil pan 12. The engine 10 can powered by a fossil fuel and be a gasoline, gasohol, or diesel engine. The engine has a engine exhaust gas outlet 14. Alternatively, but not shown the engine can have an exhaust gas manifold having a exhaust manifold outlet. There is an emission treatment device 16 selected from at least one of a catalyst, a filter, and a catalyzed filter. A suitable conduit, such as exhaust pipe 15, communicates between the exhaust gas outlet 14 and the emission treatment device 16. There is an over coat of a predetermined amount at least one poison compound, or precursor therefor, having at least one component selected from the group consisting phosphorous, zinc and sulfur.

In one embodiment of the present invention one poison compound, or precursor therefor can be fed to emission treatment device 16 from oil pan 12 through the engine 10. Alternatively, or in combination the poison compound, or precursor therefor can be fed into emission treatment device 16, preferably through a feed port 18 into the conduit 20 at a location between the exhaust gas outlet 14 or the exhaust gas manifold outlet and the emission treatment device 16. There is a means to feed, such as a pump, to feed the feed port at least one poison or a compound capable of forming the poison. Finally, there is a means, not shown, to evaluate the emission treatment device to determine the conversion percent of at least one pollutant component by the catalyst, the light-off temperature of at least one pollutant component at the catalyst, and/or the efficiency of the filter.

Figure 1A:
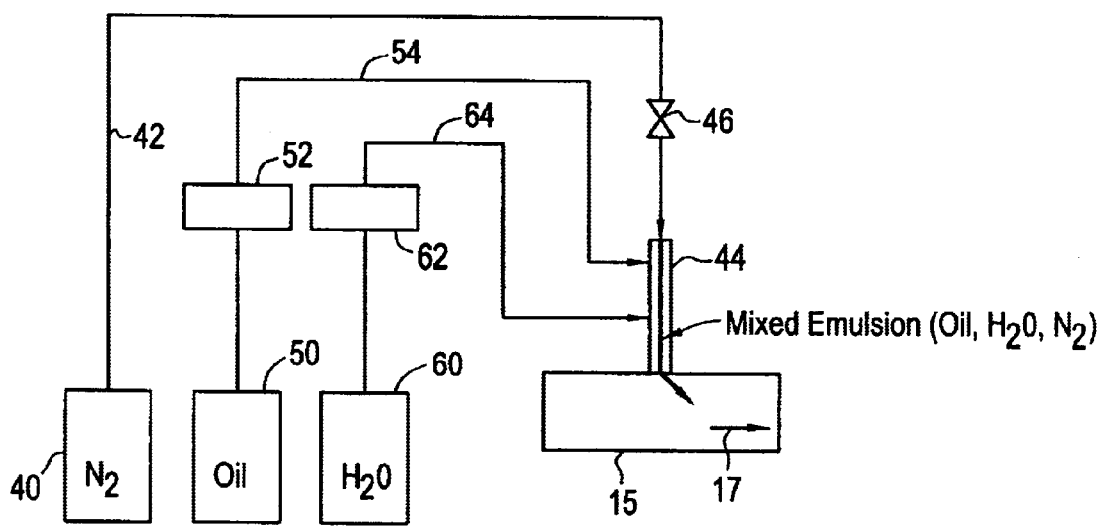
FIG. 1A is a schematic diagram of a injection system, useful to inject nitrogen, oil and water into an engine exhaust stream, upstream of the exhaust treatment catalyst.

FIG. 1A is a schematic diagram of an injection system, useful to inject an inert gas such as nitrogen, oil and water into an engine exhaust stream 17, upstream of the exhaust treatment catalyst. More particularly, nitrogen from a nitrogen reservoir 40, under a higher pressure than that in the exhaust pipe 15, is in communication, via a nitrogen conduit 42, with a mixing manifold 44 which feeds into exhaust pipe 15 upstream of the emission treatment device 16. There can be a control means, such nitrogen valve 46 to control the flow of the nitrogen to the manifold 44.

Oil from an oil reservoir 50, can be pumped by oil pump 52 under a higher pressure than that in the exhaust pipe 15, is in communication, via a oil conduit 54, with mixing manifold 44. The oil pump can control the flow of the oil to the manifold 44.

Water from an water reservoir 60, can be pumped by water pump 62 under a higher pressure than that in the exhaust pipe 15, is in communication, via a water conduit 64, with mixing manifold 44. The water pump can control the flow of the water to the manifold 44. A useful pump to pump the oil and water is an FMI brand; type QG20; with a CKC RH1 head. The mixing manifold 44 can be a suitable length and diameter of metal pipe forming a sealed enclosed surface having an outlet port in communication with the exhaust pipe 15. Preferably the manifold 44 is made of stainless steel. The length and diameter of the pipe can be varied as needed. The manifold 44 should have inlet ports whereby it is connected and in communication with gas conduit 42, oil conduit 54 and water conduit 64. A useful stainless steel manifold has an outside diameter ranging from about 1/8 to about 1 inch, and preferably about 1/4 inch. The wall thickness should be great enough to withstand the pressures and temperature of the testing environment, with a preferred wall thickness ranging from 1/16 to 1/4 inch, and preferably about 3/32 inches.

Typical poisons which are addressed include compound containing poison components such as mixtures (e.g., physically mixed compounds), chemical compound compositions (e.g., molecules containing), and combinations thereof. The specific poisons of most concern comprise individually or in combination one or more of phosphorous, zinc and/or sulfur components. The compounds to which the present invention is directed can be the poison compound which ultimately poison an emission treatment device or precursor's therefor.

Typically, the source of the poison compounds is in lubricating oils, although they can have other sources such as the sulfur compounds present in diesel fuel or in gasoline. The at least one poison compound can be selected from the group of a compounds comprising phosphorous, a compound comprising zinc compound, a sulfur compound, a compound comprising phosphorous and zinc, a compound comprising zinc and sulfur and a compound comprising phosphorous zinc and sulfur.

Specific poison compounds comprising phosphorous are selected from the group consisting of ammonium hydrophosphate, phosphoric acid, phosphorus acid, and organo phosphorus compounds. Organic phosphorous compounds include phosphines, phosphoranes, phosphonium salts. Other phosphorous compounds include phosphorous sulfides and phosphorous halides.

The compound comprising zinc can be selected from the group consisting of zinc oxide, zinc nitrate, zinc sulfate, zinc carbonate and organo zinc compounds. Organic zinc compounds include zinc ester salts, zinc sulfonates.

The compound comprising phosphorous and zinc can be selected from the group consisting of a mixture of zinc oxide and ammonium hydrophosphate, zinc dithio phosphate, and zinc phosphate.

Sulfur compounds can include a wide variety of sulfides, sulfates and sulfonate, as well as sulfonic acids and their derivatives.

The method of the present invention is directed to simulating the poisoning and deactivation of an emission control device selected from at least one of a catalyst and a filter. The method has two approaches. The first approach is to combine a poison compound and an emission control device to form a simulated poisoned device. The second approach is to engine age the device with an engine having oil in the oil pan with increased amounts of the poison or poison precursor compounds. Alternatively, in accordance with the second approach the poison or poison precursor compounds can be feed, preferably in combination with oil, directly into the device or into an exhaust conduit leading to the device.

The first approach can be conducted by directly adding the poison compound or poison precursor directly on to a device. This can be accomplished by combining the emission treatment device with a predetermined amount of at least one poison compound or precursor compound having at least one component selected from the group consisting phosphorous, zinc and sulfur. The poison or poison precursor can be applied directly to the emission treatment device.

The device can then be calcined. The poisoned emission treatment device is heated at suitable temperatures, typically from about 200° C. to about 1100° C., preferably from about 300° C. to about 800° C., more preferably from about 300° C. to about 500° C., most preferable about 400° C. for a sufficient time to calcine poisoned device. Typically the calcination time is from about 0.5 hours to about 24 hours preferably from about 1.0 hours to about 12 hours, more preferably from about 2.0 hours to about 8.0 hours, most preferable from about 3.0 hours to about 6.0 hours to form a calcined emission treatment device. The activity of the calcined emission treatment device can then be evaluated.

Where the device is a filter or catalyzed substrate the poison or poison precursor can be coated with a solution or slurry, sprayed, or deposited by other suitable methods. The poisoned device can then be evaluated. In preferred embodiments, catalyzed substrates are coated with a slurry containing the poison or poison precursor. The coated substrate can be calcined, if necessary, and then evaluated. This provided a rapid way to screen the effect of poisons on various catalyst compositions. The method is particularly useful to evaluate the catalysts useful as gaseous emissions exhaust catalyst. Such catalysts typically are used to treat at least one pollutant component selected from the group consisting of carbon monoxide, hydrocarbons and nitrogen oxides, volatile organic components and dry soot.

The first approach results in an article, an emission treatment device, selected from at least one of a catalyst and a filter. The emission treatment device has an over coat of a predetermined amount at least one poison or poison precursor compound having at least one component selected from the group consisting phosphorous, zinc and sulfur.

Where the article comprises an exhaust treatment catalyst. The catalyst comprises a composition having a support and at least one platinum group metal component selected from the group consisting of platinum, rhodium, ruthenium and iridium components.

Figure 13:
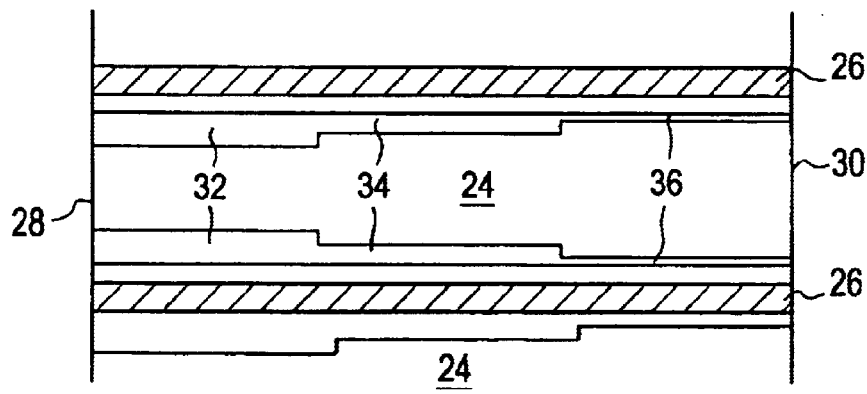
FIG. 13 is a schematic cross-sectional view of a catalyzed substrate channel with a poison coating on the catalyst in zones of poison from the inlet to the outlet.

In a specific embodiment referred to in FIG. 13, the article comprises a catalyst supported on a substrate 22 such a flow through catalyzed substrate, or wall flow filter which is optionally catalyzed, each having channel 24 defined by channel walls 26 (in the case of a wall flow filter the channel is blocked on one end) extending from an inlet end 28 to an outlet end 30 and the poison compound or precursor is deposited in varying concentrations from the inlet to the outlet. The poison can be deposited in zones 32, 34 and 36 having different concentrations and/or loading amounts from the inlet to the outlet. The poison is preferably deposited in an inlet zone 32 having a higher concentrations or loadings then at the downstream zone 34 or the outlet zone 36 located between the inlet zone and the outlet end.

The poison compound or poison precursor can be deposited in discreet zone based on loadings or concentrations or in gradients from the inlet end 28 to the outlet end 30. Methods to zone coat the poison compound or poison precursor compound are analogous to zone coating catalysts and related materials on to monolithic honeycombs. Reference is made to such methods disclosed in commonly assigned U.S. Ser. No. 09/067,820, entitled Layered Catalyst Composite and published as WO 99/55459 all herein incorporated by reference.

Other useful methods of zone coating for the present invention are known. Such methods for zone coating monolithic honeycombs containing different catalyst compositions in zones along the length of the honeycomb are also known for use in catalytic combustion processes from references such as WO 92/09848 herein incorporated by reference. It is disclosed that graded catalyst structures can be made on ceramic and metal monoliths by a variety of processes. Monoliths can be partially dipped in washcoat and excess washcoat blown out of the channel. The process is repeated by dipping further into the washcoat sol. Alternatively, catalyst is disclosed to be applied to metal foil which is then rolled into a spiral structure. The washcoat is disclosed to be sprayed or painted onto the metal foil or applied by other known techniques such as by chemical vapor deposition, sputtering, etc.

The second approach is to engine age the device with an engine having oil in the oil pan with increased amounts of the poison or poison precursor compounds. In accordance with this approach the emission treatment device can be combined with poisons provided by a the operation of a gasoline or diesel engine, having an exhaust gas outlet or an exhaust gas manifold outlet. The engine can be on a bench stand in the laboratory or on a motor vehicle. An exhaust gas stream comprising pollutants selected at least one pollutant component selected from the group consisting of carbon monoxide, hydrocarbons and nitrogen oxides, volatile organic components and dry soot, from the exhaust gas outlet or the exhaust gas manifold outlet of the engine is passed to the emission treatment device. At least one poison compound having at least one component selected from the group consisting phosphorous, zinc and sulfur can be added to the exhaust gas stream at a location between the exhaust gas outlet or the exhaust gas manifold outlet and the emission treatment device. The exhaust gas containing the poison compound can then contact the emission treatment device to form a poisoned emission treatment device. The emission treatment device can then be evaluated.

In another embodiment of the second approach, the gasoline or diesel engine have an oil pan in which lubricating oil is located. At least one poison compound having at least one component selected from the group consisting phosphorous, zinc and sulfur is added to the oil in an amount in excess of the amount functionally required for the oil to function. The emission treatment device can then be evaluated.

In the second approach, the level of poison such as ZDDP and the amount of oil injected can be varied, depending upon the degree of deactivation required. The engine is then run through a combination of high speed and load (to thermally deactivate the catalyst), and low speed/low load conditions combined with injection of the oil into the exhaust stream (to deposit the poisons on the catalytic surface). This combination of high and low temperature operation is run cyclically, until the desired level of deactivation is achieved.

In an alternative and preferred embodiment, the emission treatment device can be combined with at least one poison compound or precursor compound having at least one component selected from the group consisting phosphorous, zinc and sulfur. The poison or poison precursor can be applied directly to the emission treatment device. The device can then be calcined. Where the device is a filter or catalyzed substrate the poison or poison precursor can be coated with a solution or slurry, sprayed, or deposited by other suitable methods. The poisoned device can then be evaluated.

The step of evaluating the catalytic activity of the gaseous emissions exhaust catalyst comprises contacting a synthetic gas comprising at least one pollutant component with the poisoned catalyst at predetermined conditions of temperature, time and pollutant component concentration to determine the conversion percent of at least one pollutant component and/or the light-off temperature of at least one pollutant component. The catalyst can have poison added at a predetermined rate. Catalyst light off is the temperature at which 50% conversion of a given pollutant is converted. This can be determined using flame ionization detector to measure hydrocarbon conversion. Carbon monoxide conversion can be measured using nondispersive infrared (NDIR) analysis. Nitrogen oxide conversion can be determined using a chemiluminescence analyzer. Pressure drop, weight game, micro photographs can be used to assess the effect of poison as becoming a barrier to a filter. It is recognized that such methods of analysis are well know in the emissions treatment art.

In accordance with the method of the present invention when using the system of FIG. 1A, the emission treatment device 16 (e.g., the catalyst) to be aged is mounted on an engine test bench. The lubricating oil in the engine 10 may be doped with high levels of catalyst poison or poison precursor such as zinc dialkyl dithiophosphate (ZDDP), a commercially available phosphorus/Zinc/Sulfur compound. Alternatively or in combination, an apparatus can be set up to inject ZDDP-containing engine oil directly into the exhaust stream, upstream of the catalytic converter 16. The level of ZDDP and the amount of oil injected can be varied, depending upon the degree of deactivation required. Factors to consider include the conditions of testing such as engine operating conditions (e.g. engine speed and engine load), and the type of oil and poisoning compounds to be studied. The engine can then run through a combination of high speed and load (to thermally deactivate the catalyst), and low speed/low load conditions combined with injection of the oil into the exhaust stream (to deposit the poisons on the catalytic surface). This combination of high and low temperature operation is run cyclically, until the desired level of deactivation is achieved. In general, exhaust gas temperatures during accelerated aging on an engine dynamometer or a laboratory reactor can be vary, from about 300° C. during low load and low speed operation, and up to about 1200° C. during high load and high speed operation. More specifically, the exhaust gas temperatures can be vary, in the range of 300° C. to 1200° C. Alternatively, operating ranges can be from about 300° C. to about 600° C. during low speed and low load operation, or from about 600° C. to about 1200° C. during high speed and high load operation.

The present invention includes a method of introducing the poison-containing oil in to the exhaust stream 17. The process of introducing engine lubricating oil (with or without elevated levels of poisonous compounds) is critical. For instance, if oil is dripped or injected, preferably as a mist using a nozzle, into the exhaust stream, it could coke or oxidize at the point of introduction, and may 1) never reach the catalyst washcoat surface, or 2) coke and block the nozzle or other device used to drip or inject the oil in to the exhaust stream.

In accordance with the method of the present invention, coking of oil in the process of accelerated aging of a catalytic converter on an engine dynamometer or a laboratory reactor is prevented or minimized. Forcing the oil into the exhaust stream as a mist with the assistance of high pressure nitrogen or other inert gas is one embodiment of the present invention. This assists in keeping the flow nozzle clear during certain types of catalyst aging.

Another embodiment of this invention is the introduction of both high pressure nitrogen (or other inert gas) and water with the oil. The water can be dripped or sprayed into the manifold. Preferably, the water introduced as a mist using a nozzle. The oil, water and nitrogen have to be introduced at predetermined rates and pressures, sufficient to keep a clear flow through the injection nozzle or orifice. This method results in the emulsification of the oil by the water. As the mixture comes in contact with the hot walls of the injector and tube, some coking will begin. However, the water in the emulsion evaporates at these temperatures, and thus cleans out the oil flow passage. This self-cleaning mechanism is critical to keeping a continuous flow of oil into the exhaust gas stream for the entire duration of oil injection during certain arduous the accelerated aging test protocol.

Depending the testing protocol, including engine operation conditions, and the type of engine and exhaust system the nitrogen pressure can be from about 4 to about 100 psig, and typically varied between 4 and 20 psig, with a corresponding flow rate typically ranging between 0.2 SCFM and 1.2 SCFM. The oil injection can typically be varied between 10 and 100 cc/hr, and specifically between 20 and 50 cc/hr. The water is injected at a rate typically varying between 0 and 200 cc/hr. Specifically, between 40 and 100 cc/hr.

The method and apparatus of the present invention are particularly useful when the emission treatment device comprises a catalyst supported on a substrate. In preferred embodiments the catalyst comprises a catalyst composition comprising a support; and at least one catalytic material selected from the group consisting of at least one platinum group metal component, gold and silver. The platinum group metal component can be selected from at least on component selected from the group consisting of platinum, palladium, rhodium, ruthenium and iridium.

The present invention is particularly useful to simulate catalyst poisoning of motor vehicle catalysts and filters including catalytic filters.

Useful diesel engine emission treatment filters include wall flow filters which may or may not be catalyzed. Oxidation catalysts comprising a platinum group metal dispersed on a refractory metal oxide support are known for use in treating the exhaust of diesel engines in order to convert both HC and CO gaseous pollutants and particulates, i.e., soot particles, by catalyzing the oxidation of these pollutants to carbon dioxide and water. Reference is made to commonly assigned U.S. Ser. No. 09/191,603 herein incorporated by reference for a review of diesel catalysts and a disclosure of substrates useful to treat diesel engine exhaust emissions.

Catalyzed soot filters are known from references such U.S. Pat. Nos. 4,510,265 and 5,100,632. These references disclose the use of catalyzed soot filters in diesel exhaust streams. Reference is also made to SAE Technical Paper Series No. 860298, update on the evaluation of diesel particulate filters for underground mining by A. Lawson, et al.

Many references disclose the use of wallflow filters which comprise catalysts on or in the filter to filter and burn off filtered particulate matter. A common construction is a multi-channel honeycomb structure having the ends of alternate channels on the upstream and downstream sides of the honeycomb structure plugged. This results in checkerboard type pattern on either end. Channels plugged on the upstream or inlet end are opened on the downstream or outlet end. This permits the gas to enter the open upstream channels, flow through the porous walls and exit through the channels having open downstream ends. The gas to be treated passes into the catalytic structure through the open upstream end of a channel and is prevented from exiting by the plugged downstream end of the same channel. The gas pressure forces the gas through the porous structural walls into channels closed at the upstream end and opened at the downstream end. Such structures are primarily disclosed to filter particles out of the exhaust gas stream. Often the structures have catalysts on or in the substrate which enhance the oxidation of the particles. Typical patents disclosing such catalytic structures include U.S. Pat. Nos. 3,904,551; 4,329,162; 4,340,403; 4,364,760; 4,403,008; 4,519,820; 4,559,193 and 4,563,414.

A useful motor vehicle catalyzed substrate include three-way catalysts designed to oxidize hydrocarbons and carbon monoxide, and to reduce nitrogen oxides. Useful catalysts and catalyst structures are disclosed in WO95/35152, WO95/00235 and WO96/17671, and U.S. Pat. Nos. 4,714,694 and 5,057,483 hereby incorporated by reference.

Such catalysts can be in the form of a catalyst composition supported on a substrate such as a ceramic or metal monolith. The catalyst can be a coating on the substrate of one or more catalyst composition layers. Useful catalyst compositions can be in the form of one or more coatings. A useful and preferred catalytically active components are precious metals, preferably a platinum group metal and a support for the precious metal. Useful catalytically active components include at least one of palladium, platinum, rhodium, ruthenium, and iridium components, with platinum, palladium and/or rhodium preferred. Precious metals are typically used in amounts of up to 300 g/ft$^3$, preferably 5 to 250 g/ft$^3$ and more preferably 25 to 200 g/ft$^3$ depending on the metal.

Preferred supports are refractory oxides such as alumina, silica, titania, and zirconia. A catalyst system useful with the method and apparatus of the present invention comprises at least one substrate comprising a catalyst composition located thereon. The composition comprises a catalytically active material, a support and preferably an oxygen storage component.

The platinum group metal component support components useful in the composition of the present invention includes at least one stabilized refractory compound, which is most preferably lanthana stabilized alumina, and additionally at least one unstabilized refractory compound selected from the group consisting of silica, alumina and titania compounds. Preferred first and second supports which are not stabilized compounds can be activated compounds selected from the group consisting of alumina, silica, titania, silica-alumina, alumino-silicates, alumina-zirconia, aluminachromia, and alumina-ceria. In the composite of the present invention at least one of the first and second layer, preferably the first layer comprises at least one stabilized refractory compound, which is most preferably lanthana stabilized alumina, and additionally at least one refractory compound selected from the group consisting of silica, alumina and titania compounds. The other layer, preferably the second layer comprises at least one of the recited unstabilized refractory oxide supports.

Preferred oxygen storage components useful in these catalysts have oxygen storage and release capabilities. The oxygen storage component is any such material known in the art, preferably at least one oxide of a metal selected from the group consisting of rare earth metals, and most preferably a cerium or praseodymium compound, with the most preferred oxygen storage component being cerium oxide (ceria). The oxygen storage component can be present at least 5 wt. % and preferably at least 10 wt. % and more preferably at least 15 wt. % of the catalyst composition.

These catalysts may further contain a nickel or iron component to suppress hydrogen sulfide. Stabilizers can be in either the first or second layers, and are preferably in the first layer. Stabilizers can be selected from at least one alkaline earth metal component derived from a metal selected from the group consisting of magnesium, barium, calcium and strontium, preferably strontium and barium. Zirconium components in the first and/or second layers is preferred and acts as both a stabilizer and a promoter. Rare earth oxides act to promote the catalytic activity of the first layer composition. Rare earth metal components are preferably selected from the group consisting of lanthanum metal components and neodymium metal components.

For typical automotive exhaust gas catalytic converters, the catalyst composite which includes a monolithic substrate generally may comprise from about 0.50 to about 6.0, preferably about 1.0 to about 5.0 g/in$^3$ of catalytic composition coating.

When the compositions, including the poison compounds or precursors thereof of the present invention, are applied as one or more thin coatings to a monolithic carrier substrate, the proportions of ingredients are conventionally expressed as grams of material per cubic inch of catalyst as this measure accommodates different gas flow passage cell sizes in different monolithic carrier substrates. Platinum group metal components are based on the weight of the platinum group metal.

Any suitable substrate, also referred to as a carrier, may be employed, such as a monolithic carrier of the type having a plurality of fine, parallel gas flow passages extending therethrough from an inlet or an outlet face of the carrier, so that the passages are open to fluid flow therethrough (see above discussion regarding wall flow carriers). The passages, which are essentially straight from their fluid inlet to their fluid outlet, are defined by walls on which the catalytic material is coated as a "washcoat" so that the gases flowing through the passages contact the catalytic material. The flow passages of the monolithic carrier are thin-walled channels which can be of any suitable cross-sectional shape and size such as trapezoidal, rectangular, square, sinusoidal, hexagonal, oval, circular. Such structures may contain from about 60 to about 600 or more gas inlet openings ("cells") per square inch of cross section. The ceramic carrier may be made of any suitable refractory material, for example, cordierite, cordierite-alpha alumina, silicon nitride, zircon mullite, spodumene, alumina-silica magnesia, zircon silicate, sillimanite, magnesium silicates, zircon, petalite, alpha alumina and aluminosilicates. The metallic honeycomb may be made of a refractory metal such as a stainless steel or other suitable iron based corrosion resistant alloys.

Such monolithic carriers may contain up to about 700 or more flow channels ("cells") per square inch of cross section, although far fewer may be used. For example, the carrier may have from about 60 to 600, more usually from about 200 to 400, cells per square inch ("cpsi").

The discrete form and second coats of catalytic material, conventionally referred to as "washcoats", as well as the poison compounds of the present invention, can be coated onto a suitable carrier with, preferably, the first coat adhered to the carrier and the second coat overlying and adhering to the first coat. With this arrangement, the gas being contacted with the catalyst, e.g., being flowed through the passageways of the catalytic material-coated carrier, will first contact the second or top coat and pass therethrough in order to contact the underlying bottom or first coat. However, in an alternative configuration, the second coat need not overlie the first coat but may be provided on an upstream (as sensed in the direction of gas flow through the catalyst composition) portion of the carrier, with the first coat provided on a downstream portion of the carrier. Thus, to apply the washcoat in this configuration, an upstream longitudinal segment only of the carrier would be dipped into a slurry of the second coat catalytic material, and dried, and the undipped downstream longitudinal segment of the carrier would then be dipped into a slurry of the first coat catalytic material and dried.

Alternatively, separate carriers may be used, one carrier on which the first coat is deposited and a second carrier on which the second coat is deposited, and then the two separate carriers may be positioned within a canister or other holding device and arranged so that the exhaust gas to be treated is flowed in series first through the catalyst containing the second coat and then through the catalyst containing the first coat thereon. However, as indicated above, it is preferred to utilize a catalyst composition in which the second coat overlies and adheres to the first coat because such configuration is believed both to simplify production of the catalyst composition and to enhance its efficacy.

As indicated above, the catalyst composition, and poison compounds, of the present invention can be in the form of a pellet or in the form of layer supported on a substrate. The preferred substrate is a honeycomb catalyst carrier which can be made of metal or ceramic. The composition, in the form of a layer, can be supported on the substrate. A slurry of the composition can be used to coat a macrosize carrier. The catalyst composition can be coated as a layer on a monolithic substrate generally which can comprise a loading of from about 0.50 to about 6.0, preferably about 1.0 to about 5.0 g/in$^3$ of catalytic composition based on grams of composition per volume of the monolith.

The present invention is illustrated further by the following examples which are not intended to limit the scope of this invention. Various of the Examples include microprobe X-ray maps of a cross-section of catalyst coated ceramic honeycomb walls. When viewing the maps in black and white, the lighter areas are an indication of catalyst composition poisons (e.g. phosphorous or zinc compounds).

EXAMPLES

Laboratory Method for Zn—P Poisoning of TWC Catalyst

Example 1

Reference Catalyst A.

Reference catalyst A is a typical TWC catalyst with a Pd loading of 130 g/ft$^3$. It is a two layered catalyst with the bottom layer having 0.43 g/in$^3$ of Pd supported on alumina and additionally g/in$^3$ of alumina, 0.26 g/in$^3$ of a ceria/zirconia composite, 0.62 g/in$^3$ of ceria, 0.2 g/in$^3$ of zirconia, 0.09 g/in$^3$ of BaO, 0.06 g/in$^3$ Nd$_2$O$_3$, 0.09 g/in$^3$ La$_2$O$_3$, 0.92 g/in$^3$ NiO; and a top layer having 0.70 g/in$^3$ of Pd supported on alumina, 0.2 g/in$^3$ of a ceria/zirconia composite, 0.1 g/in$^3$ of zirconia, 0.10 g/in$^3$ Nd$_2$O$_3$, 0.10 g/in$^3$ La$_2$O$_3$, 0.1 g/in$^3$ of SrO. The two layered catalyst was supported on a ceramic honeycomb substrate having 400 cells per square inch, and being 3 inches long with a racetrack shape. The catalyzed honeycomb was oven aged in dry air at 750° C. for 4 hours before modification using the zinc-phosphorous poisoning.

Example 2

Zn—P Modification Method Catalyst B 20 g of ZnO was made into a slurry by adding water to about 150 g. The slurry was mixed for about 30 minutes. 12 g of the diammonium hydrogen phosphate was added to 56 g of the ZnO slurry. The addition of the phosphate component made the ZnO a coat-able slurry. The Zn—P slurry was then coated over cores of the aged catalyst A to make a wash coat loading of about 0.5 g/in3. The ZnO and P205 concentration based on total weight of substrates and wash coat was about 3.2 and 6% respectively. After coating the catalyst was dried and calcined at 550° C. for 2 hrs.

Figure 2:
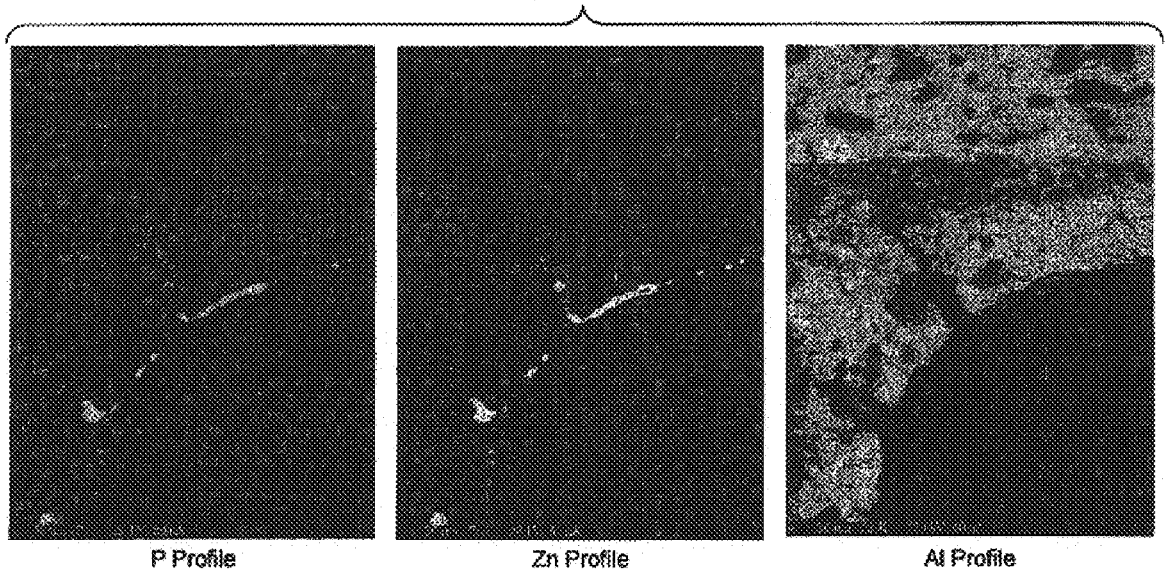
FIG. 2 is a microprobe X-ray map of zinc and phosphorus fresh as deposited on surface of washcoat in Example 2.
Figure 3:
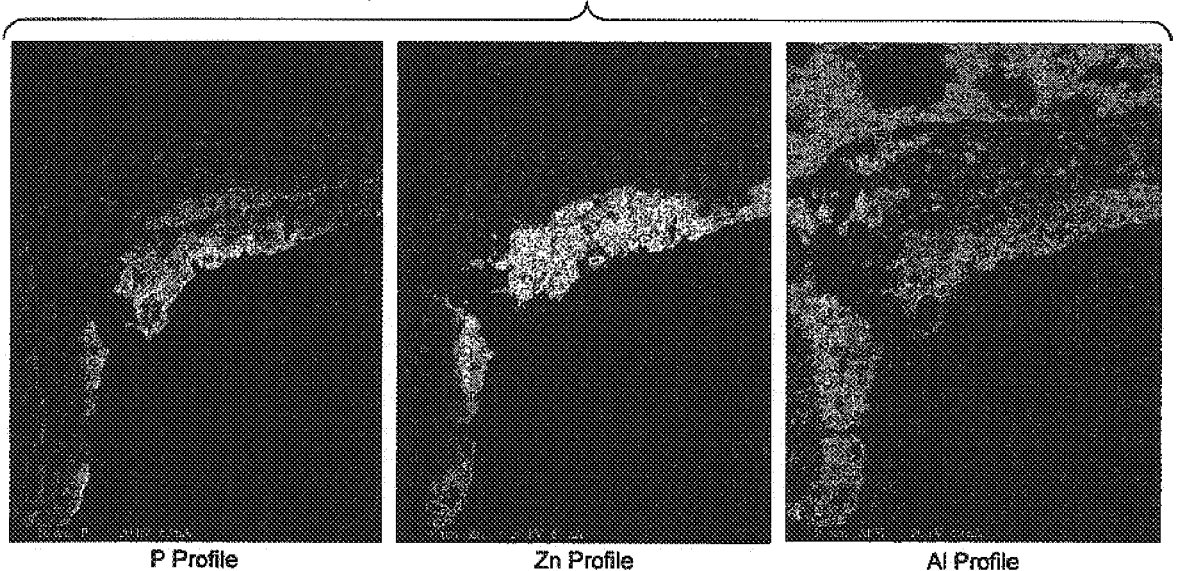
FIG. 3 is a microprobe X-ray map of zinc and phosphorus profiles after 1050C aging in air in Example 2.
Figure 4:
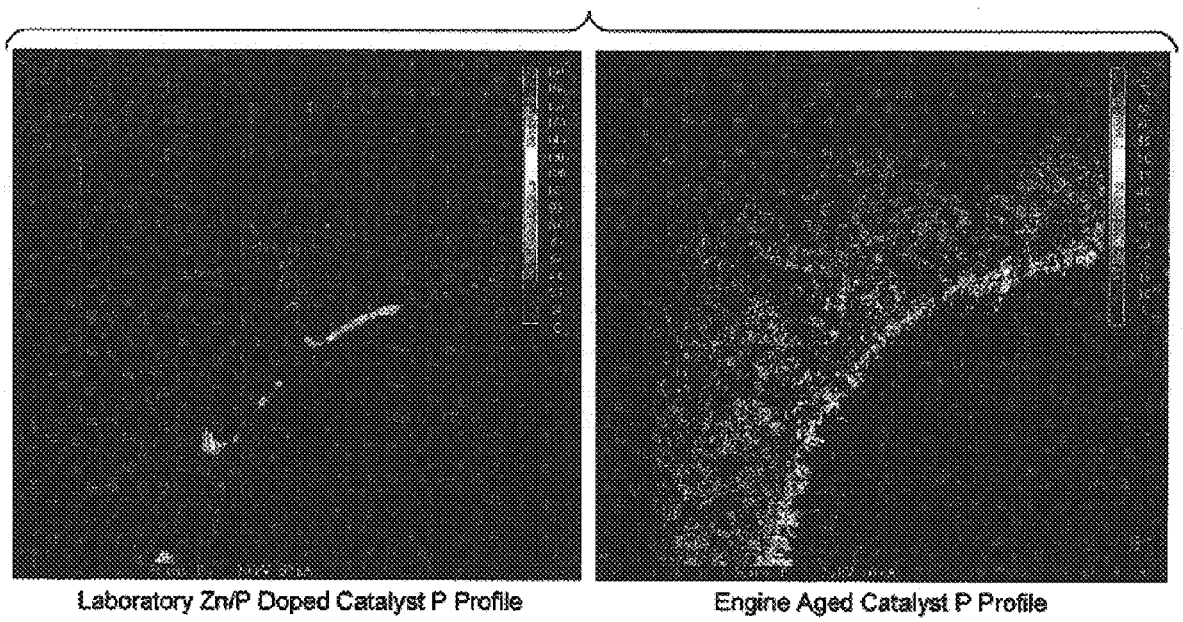
FIG. 4 is a microprobe X-ray map of samples showing laboratory tested versus engine tested phosphorus profiles in Example 2.

Microprobe, X-ray maps, of the Zn—P poisoned catalysts showed a clear layer of Zn—P on the surface of the catalyst, especially at the top layer. An alumina coated sample is used as a reference. See FIGS. 2 and 3. This was the case for the Zn—P poisoned catalyst measured fresh or after 1050° C. aging. The X-ray maps of the ZnO and P lab prepared samples resemble to great extent the engine poisoned samples using lubricant containing predetermined amount of Zn and P. FIG. 4 shows the comparison between an engine-aged catalyst Phosphorus profile and that of a laboratory-prepared Zn/P doped catalyst.

Example 3

Testing Procedure:

The hydrocarbon oxidation activity of the reference catalysts and the Zn—P poisoned catalysts were measured as fresh and aged. The 750° C. conditioned catalysts was considered fresh. These catalysts were also oven aged at 1050° C. in dry air for 4 hrs. (Aged catalyst).

The catalysts were evaluated in a mini-reactor using cored samples from the above referenced substrates (the cores had a diameter=0.5 cm and length=2.5 cm). The hydrocarbon conversion activity was measured in a temperature ramp up from 150 to 550° C. The gas composition is made up of propene=200 PPM, propane=200 PPM, methane=100 PPM, $O_2$=5%, NO=500 PPM, 10% steam, and balance $N_2$. The conversion was measured at a space velocity of 50,000/hr.

Example 4

Figure 5:
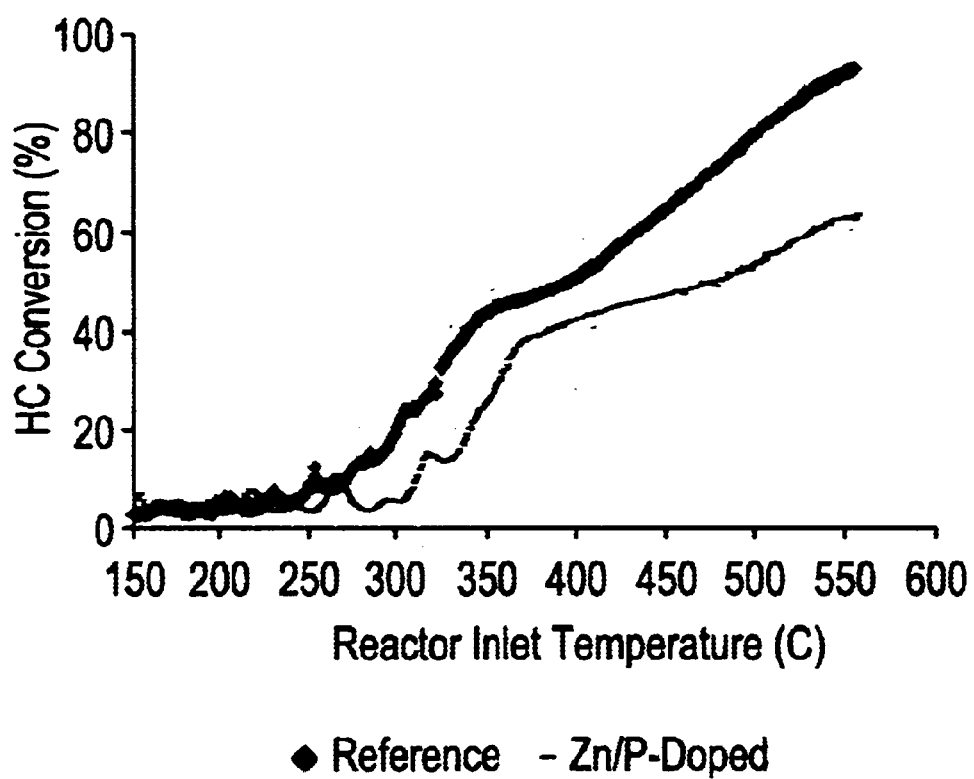
FIG. 5 is a graph showing a reference sample versus Zn/P doped catalyst sample in a lab reactor light off test comparison in Example 4.

Comparison of Fresh Reference and Poisoned Catalysts:

Catalyst B prepared by addition of Zn—P to catalyst A (poisoned by the procedure outlined above) showed severe deactivation for hydrocarbon conversion activity (FIG. 5). This is similar to the vehicle aged catalysts in real applications. Therefore, by using a simple laboratory procedure we were able to mimic ZnO—P poisoning of catalytic converter on vehicles after extended driving (over 100,000 miles). This approach for the Zn—P poisoning should allow for the simulation of catalytic converter poisoning in a laboratory environment with minimal cost.

Figure 6:
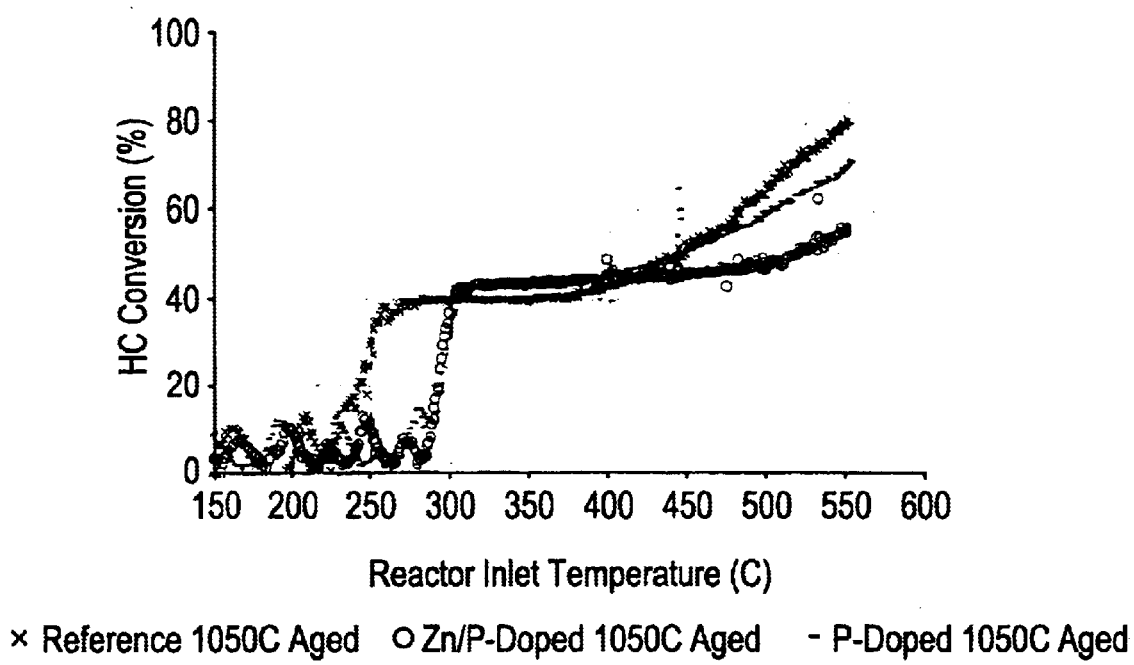
FIG. 6 is a graph showing a reference sample and Zn/P doped catalyst sample in a lab reactor light off text after 1050C aging in Example 4.

The ZnO—P modified catalyst B was also aged at 1050° C. and the results of hydrocarbon conversion activity was compared to unmodified reference catalyst A in FIG. 6. The results again show the severe deactivation effect of the Zn—P poisoning using the lab procedure (Example 3) on the catalyst performance. After aging this method of poisoning showed again good resemblance to the Zn—P poisoned catalyst in real application. By using the Zn—P laboratory poisoning method we were able to demonstrate its use as a method to mimic real poisoning by Zn—P of the catalytic converter during actual driving and accumulation of thousands of miles. The advantage of this method is to demonstrate the ability to mimic in a lab setup, the Zn—P poisoning that occurs in vehicles after extended driving. This test would, therefore, predict the tolerability of the catalytic converters to Zn and P poisoning.

Engine Aging Method for Zn—P Poisoning of TWC Catalyst:

Example 5

Figure 7:
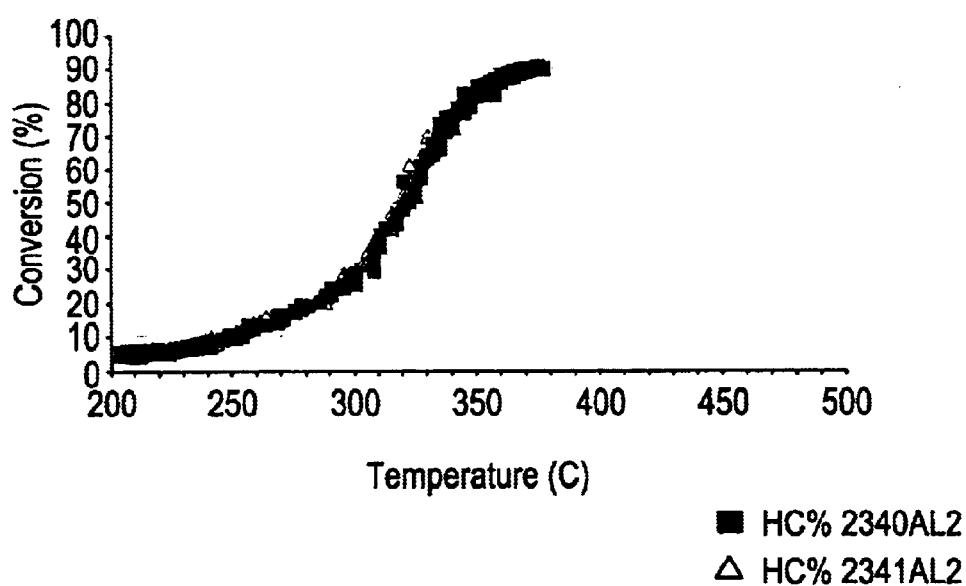
FIG. 7 is a graph showing HC light off tests on catalysts aged on exothermic cycle alone in Example 4.

Two catalyst samples, were aged on an engine for 75 hours in a cyclic exothermic aging such as that described in the SAE paper 972906 (Replication of 50 k vehicle-aged catalyst performance using an engine dynamometer aging cycle: P. Johnson, et al., October 1997). Both catalysts were of the same type, 64 cubic inches, 3.03×5.78×4.5 in., 400 cpsi and with a precious metal loading of 180 g/ft3, 2/27/1 Pt/Pd/Rh. After the high temperature aging, the catalysts were tested for light off activity on an engine bench stand, to ensure that they had been aged identically. The light off test was run with clear indolene as the fuel, a space velocity of 80,000/hr, and an air/fuel perturbation of 0.5 @ 1.0 Hz. FIG. 7 shows that the light off curves are, indeed, identical.

Figure 8:
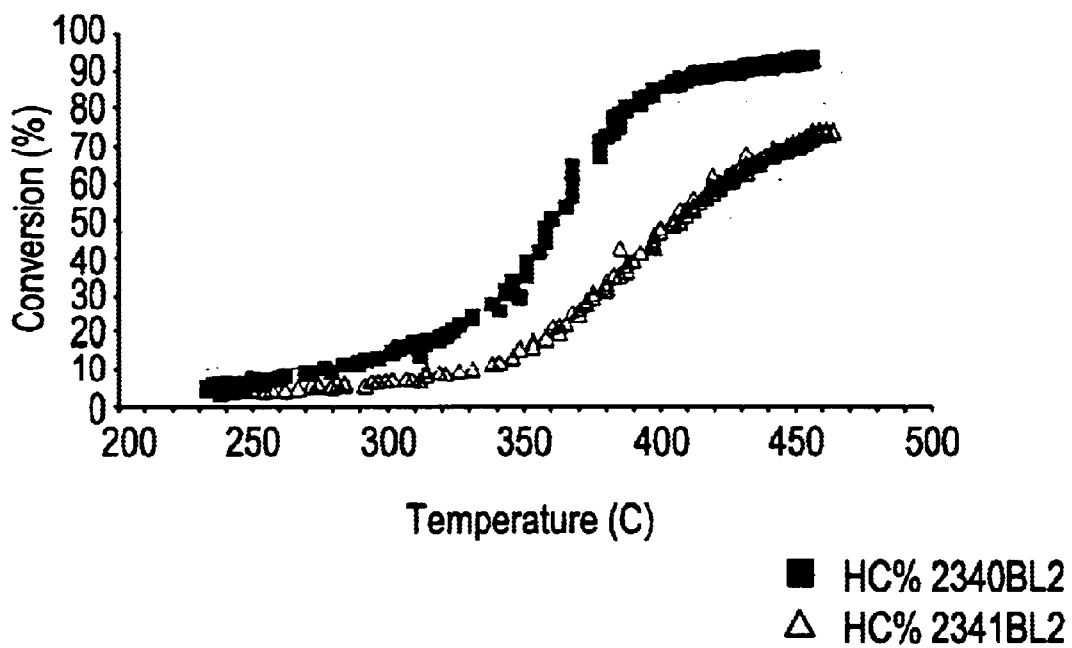
FIG. 8 is a graph showing HC light off curves with and without oil injection into exhaust stream in Example 5.

The same catalysts (Sample numbers GF02340 & GF02341) were then aged for an additional 24 hours, at 450° C. catalyst inlet temperature and steady state, with oil injected into the exhaust just ahead of sample number GF02341. The oil contained 15 times the nominal level of ZDDP as an additive. During this time, the oil flowed into the exhaust stream in a steady flow, with a total of approximately 0.75 quarts during the 24-hour period. After this poison aging, the catalysts were tested again for light off. From FIG. 8, it can be seen that both the catalysts lost activity after this low temperature aging. However, the one with the oil injection was much worse due the phosphorus poisoning effect.

Figure 9:
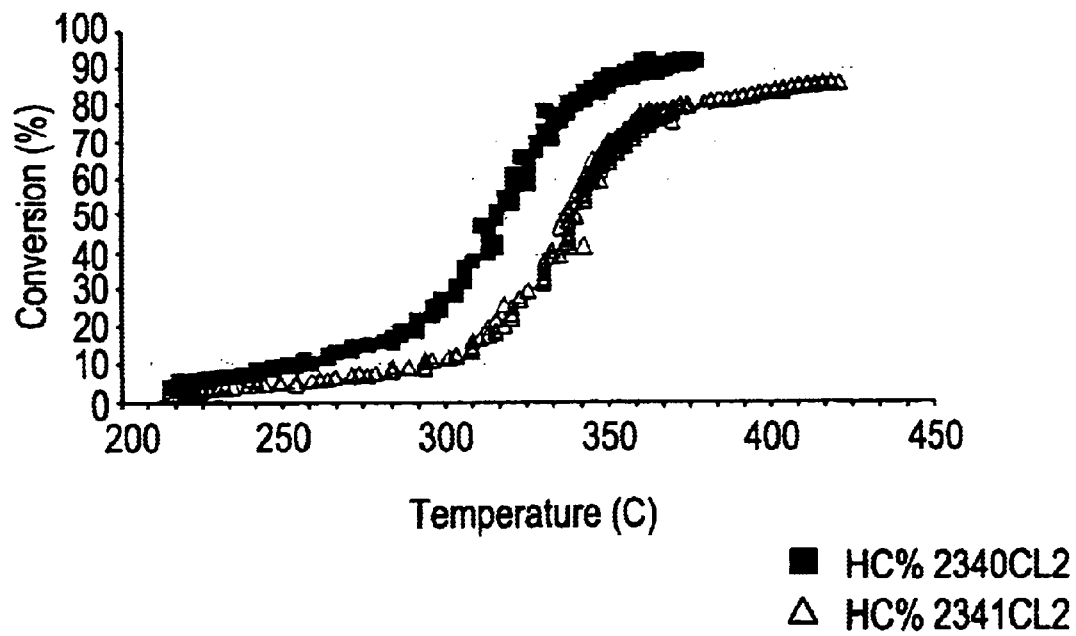
FIG. 9 is a graph showing HC light off test for catalysts aged with and without oil injection into exhaust stream in Example 5.

After the second light off, the catalysts were run at 600° C. for about 1 hour to purge them of sulfur accumulated during the aging process. Then, the catalysts were evaluated for light off again. FIG. 9 shows that GF02340 fully recovered due to the removal of sulfur. GF02341 was still poorer than GF02340, due to the effect of the poisoning due to phosphorus and zinc.

Figure 12:
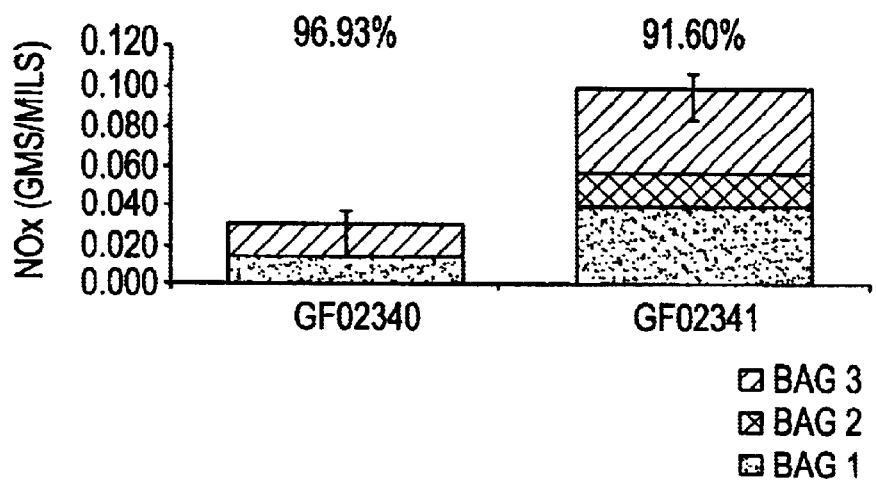
FIG. 12 is a graph showing FTP tailpipe NOx emissions for catalysts aged with and without oil injection in Example 5.

The same catalysts were then tested according to a 1975 FTP test run on a 1998 Ford Crown Victoria vehicle. The FTP 75 test is described in Title 40 Code of Federal Regulations, Part 8b (40 CFR #86) and in particular 40 CFR 86.130-78 to 86.140-82 (1987). FIG. 10 shows the tailpipe Hydrocarbon emissions for these two catalysts. Clearly, the oil injection has a detrimental effect on hydrocarbon performance of sample number GF02341. Likewise, FIG. 11 and FIG. 12 show the relative CO and NOx emissions. From all of these tests, it is clear that oil injection into the exhaust stream at low temperature results in poisoning of the catalyst.

Example 6

Figure 14:
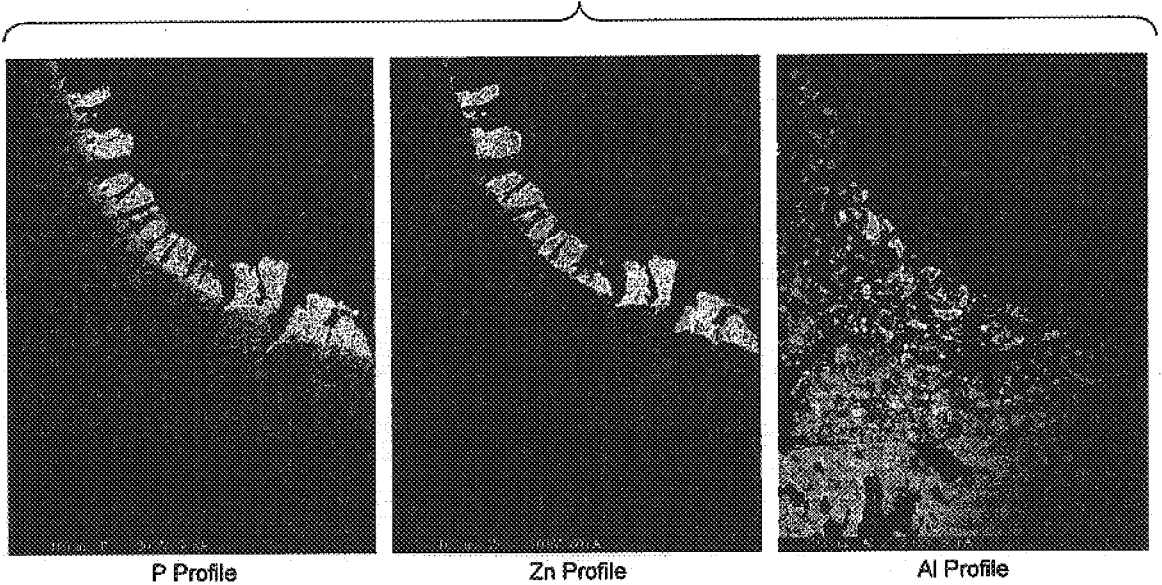
FIG. 14 is a microprobe X-ray maps of a sample showing engine tested phosphorus profiles with oil injection in Example 6.
Figure 15:
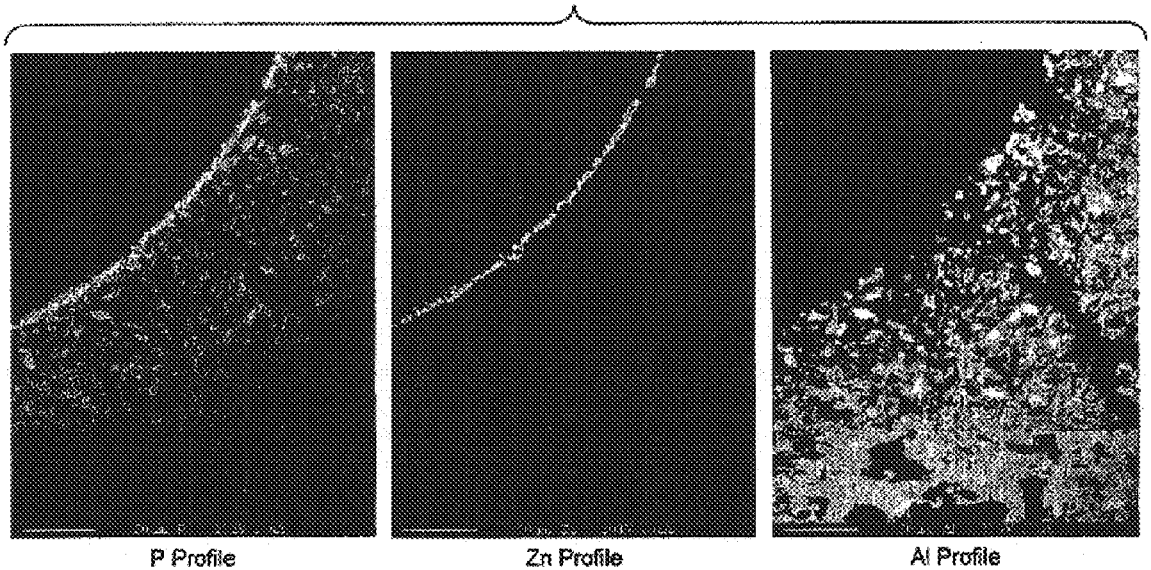
FIG. 15 is a microprobe X-ray maps of samples showing engine tested phosphorus profiles without oil injection in Example 6.

Two catalyst samples were evaluated as washcoats on ceramic honeycomb supports being 42 cubic inches, with dimensions of 2.68×5.68×3.15 inches, and having 400 cpsi (Cells per square inch). The catalyst compositions were substantially the same as in Example 1 except that they had a precious metal loading of 200 g/ft$^3$ of palladium. The supported catalysts were aged on an engine for 75 hours in a cyclic exothermic aging such as that described in the SAE paper 972906 (Replication of 50 k vehicle-aged catalyst performance using an engine dynamometer aging cycle: P. Johnson, et al., Oct 1997). After the high temperature aging step, the engine was cycled down to idle speed, and no load. Cooling fans were turned on automatically during this portion of the cycle to further cool down the catalytic converter, to either 400° C. or 600° C. After a specified period of time (20 minutes in this example), The engine was brought back to high speed and load for the next period (20 minutes in this example). This cycling of high and low speed/load was repeated for a total of 75 hours of aging. After the engine aging, the catalysts were tested for light off activity on an engine bench. The light off test was run with clear indolene as the fuel, a space velocity of 80,000/hr, and an air/fuel perturbation of 0.5 @1.0 Hz. The catalyst with oil injection was severely deactivated, compared to the catalyst that was only subjected to cyclic high temperature aging. The oil injected had DZZP level of 1.5 weight percent which is 15 times the nominal level of 0.1 weight percent. The aged catalysts were then cut open and analyzed for chemical composition and poison accumulation profiles. FIGS. 14 and 15 show the phosphorus and zinc, with alumina used as a reference, deposition profiles for the catalysts with and without oil injection. It can be clearly seen that there is a certain amount of phosphorus deposition in the catalyst washcoat from the oil consumption of the engine itself. In addition, the process of injecting oil into the exhaust results in a significant accumulation of phosphorus and other compounds on the surface of the washcoat.

This is a replication of in-field failures, where the emission control system failed prematurely, due to excessive oil consumption and accumulation of poisonous materials on the catalytic surface.

Example 7

Figure 16:
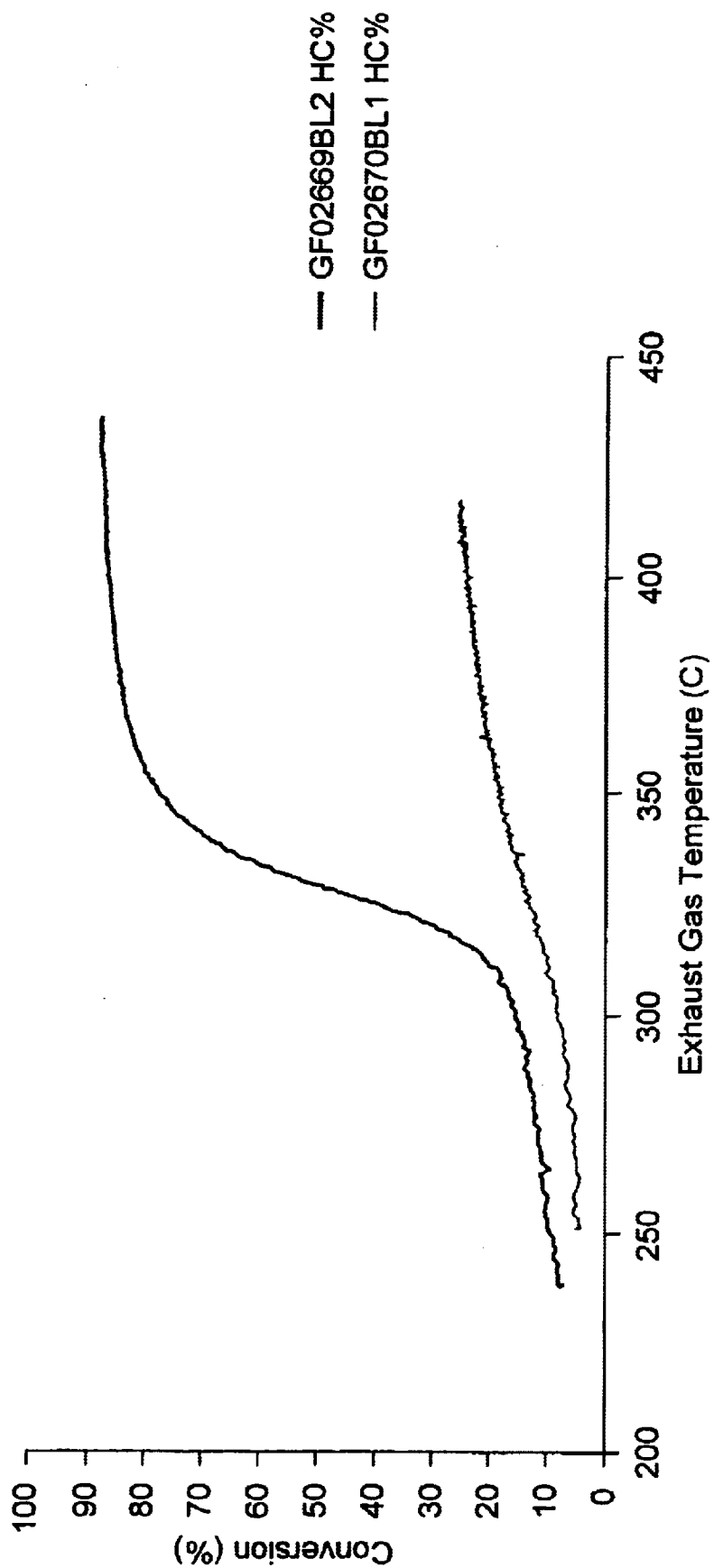
FIG. 16 is a graph showing HC light off curves with and without oil injection into exhaust stream in Example 7.

Two catalyst samples were evaluated as washcoats on ceramic honeycomb supports being 42 cubic inches, with dimensions of 2.68×5.68×3.15 inches, and having 400 cpsi (Cells per square inch). The catalyst compositions were substantially the same as in Example 1 except that they had a precious metal loading of 200 g/ft$^3$ of palladium. The supported catalysts, were aged on an engine for 75 hours in a cyclic exothermic aging such as that described in the SAE paper 972906 (Replication of 50 k vehicle-aged catalyst performance using an engine dynamometer aging cycle: P. Johnson, et al., October 1997). After the high temperature aging step, the engine was brought down to idle speed, and no load. In this example, the engine used was a 5.7 L V8 engine. During the high temperature portion, the engine was run at 2800 rpm and a manifold vacuum of 18 inches of mercury (which is an indication of the load on the engine). During the low temperature step, the engine was run at 1200 rpm and a manifold vacuum of 19 inches of mercury. Cooling fans were turned on automatically during this portion of the cycle to further cool down the catalytic converter, to 600° C. After a specified period of time (20 minutes in this example), the engine was brought back to high speed and load for the next period (20 minutes in this example). This cycling of high and low speed/load was repeated for a total of 75 hours of aging. During the entire aging, oil was injected into the exhaust stream along with water and nitrogen, at the inlet of one of the catalysts only. The nitrogen was introduced at a pressure of 15 psig and a flow rate of approximately 0.5 SCFM. The oil was pumped in at a flow rate of 40 cc/hr and the water was pumped in at a flow rate of 80 cc/hr. After the engine aging, the catalysts were tested for light off activity on an engine bench. The light off test was run with clear indolene as the fuel, a space velocity of 80,000/hr, and an air/fuel perturbation of 0.5@1.0 Hz. FIG. 16 shows that the catalyst with oil injection was severely deactivated, compared to the catalyst that was only subjected to cyclic high temperature aging.

Figure 17:
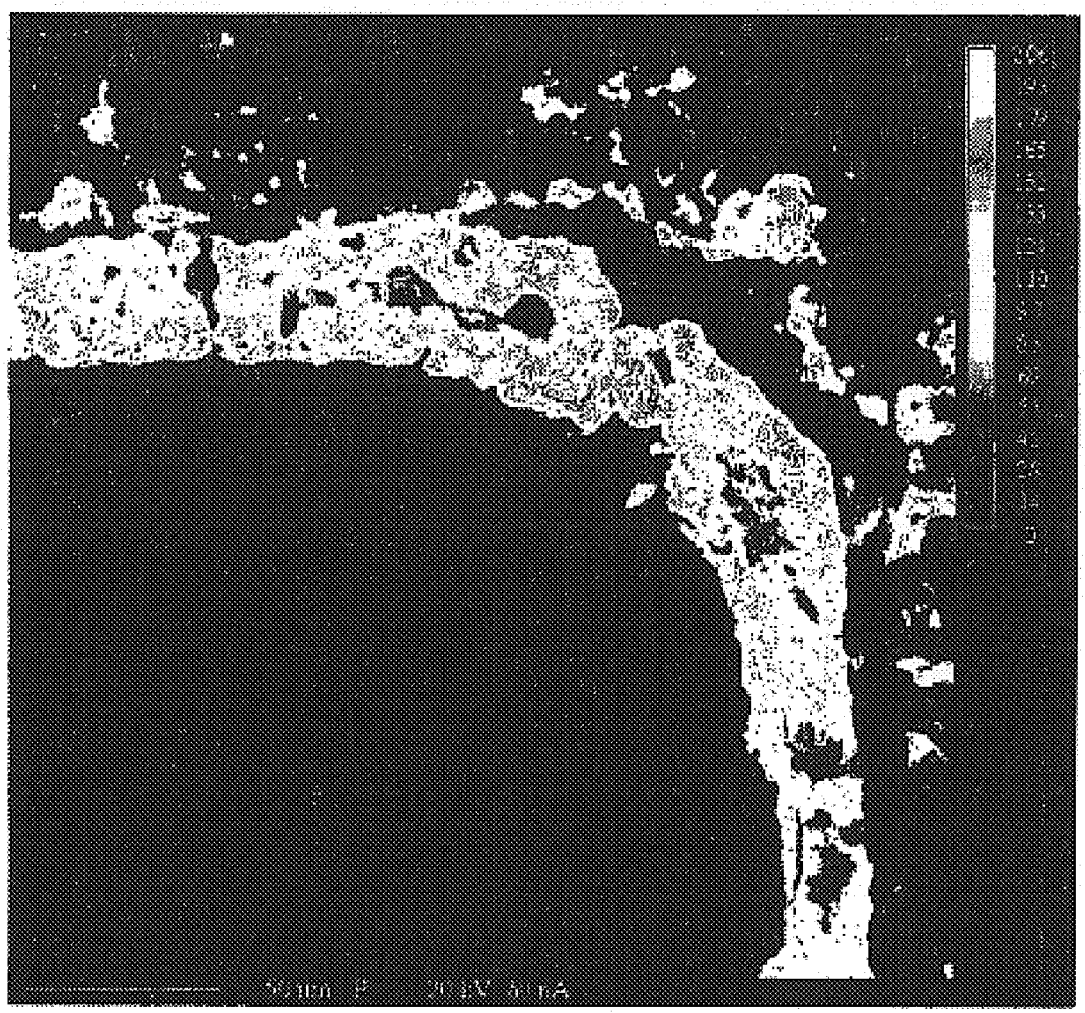
FIG. 17 is a microprobe X-ray maps of a sample showing engine tested phosphorus profiles with oil injection in Example 7.
Figure 18:
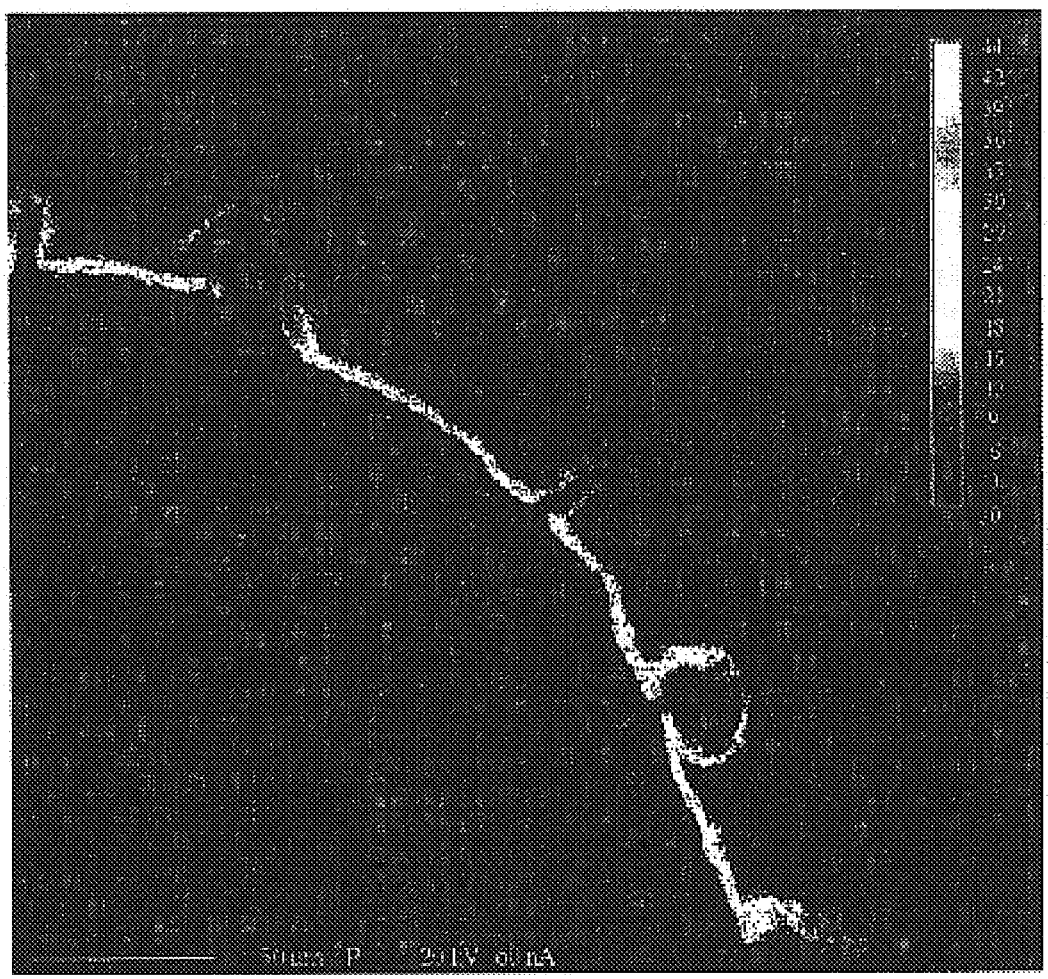
FIG. 18 is a microprobe X-ray maps of samples showing engine tested phosphorus profiles without oil injection in Example 7.

The aged catalysts were then cut open and analyzed for chemical composition and poison accumulation profiles. FIGS. 17 and 18 show the phosphorus deposition profiles for the catalysts with and without oil injection. It can be clearly seen that there is a certain amount of phosphorus deposition in the catalyst washcoat from the oil consumption of the engine itself. In addition, the process of injecting oil into the exhaust results in a significant accumulation of phosphorus and other compounds on the surface of the washcoat. This is a replication of in-field failures, where the emission control system failed prematurely, due to excessive oil consumption and accumulation of poisonous materials on the catalytic surface.

What is claimed is:

1. A method comprising the steps of:
   operating a gasoline or diesel engine, having an exhaust gas outlet or an exhaust gas manifold outlet;
   passing an exhaust gas stream comprising pollutants having at least one pollutant component selected from the group consisting of carbon monoxide, hydrocarbons and nitrogen oxides, volatile organic components and dry soot, from the exhaust gas outlet or the exhaust gas manifold outlet of the engine to an emission treatment device comprising a catalyst or a filter;
   adding to the exhaust gas stream at a location between the exhaust gas outlet or the exhaust gas manifold outlet and the emission treatment device at least one poison compound having at least one component selected from the group consisting phosphorous, zinc and sulfur;
   adding an inert gas to the poison compound;
   contacting the exhaust gas with the emission treatment device to form a poisoned emission treatment device;
   evaluating the catalytic activity of the emission treatment device to determine one or more of a conversion percent of at least one pollutant component by the catalyst, a light-off temperature of at least one pollutant component at the catalyst, or an efficiency of the filter.

2. The method as recited in claim 1 wherein the at least one poison compound is contained in an oil and the inert gas assists in forcing the oil containing poison compound into the exhaust gas stream.

3. The method as recited in claim 2 wherein the oil comprises engine oil and the oil containing poison compound enters the exhaust gas stream in the form of a mist.

4. The method as recited in claim 2 further comprising the step of adding an water to the oil containing poison compound.

5. The method as recited in claim 4 wherein the oil containing poison compound and the water are in the form of an emulsion.

6. The method as recited in claims 1 or 5 wherein the emission treatment device comprises a catalyst supported on a substrate.

7. The method as recited in claim 6 wherein the catalyst comprises a catalyst composition comprising:
   a support; and
   at least one catalytic material selected from the group consisting of at least one platinum group metal component, gold and silver.

8. The method as recited in claim 7 wherein the selected from the platinum group metal component is selected from the group consisting of platinum, palladium, rhodium, ruthenium and iridium.

9. The method as recited in claim 6 wherein the catalyst is a gaseous emissions exhaust catalyst.

10. The method as recited in claim 9 wherein the gaseous emissions exhaust catalyst is useful to treat at least one pollutant component selected from the group consisting of carbon monoxide, hydrocarbons and nitrogen oxides, volatile organic components and dry soot.

11. The method as recited in claim 6 wherein the at least one poison compound is selected from the group of a phosphorous compound, a zinc compound, a sulfur compound, a compound comprising phosphorous and zinc, a compound comprising zinc and sulfur and a compound comprising phosphorous zinc and sulfur.

12. The method as recited in claim 11 wherein:
   the phosphorous compound is selected from the group consisting of ammonium hydrophosphate, phosphoric acid, phosphorus acid, and organo phosphorus compounds;

the zinc compound is selected from the group consisting of zinc oxide, zinc nitrate, zinc sulfate, zinc carbonate and organo zinc compounds; and the compound comprising phosphorous and zinc is selected from the group consisting of a mixture of zinc oxide and ammonium hydrophosphate, zinc dithio phosphate, and zinc phosphate.

13. The method as recited in claim 12 wherein the amount of the poison compound is from about 1.0 to about 20 weight percent of the catalyst.

14. The method as recited in claim 6 wherein the step of evaluating the catalytic activity of the emission treatment device comprises contacting a synthetic gas comprising at least one pollutant component with the poisoned emission treatment device at predetermined conditions of temperature, time and pollutant component concentration to determine the conversion percent of at least one pollutant component and/or the light-off temperature of at least one pollutant component.

15. The method as recited in claim 6 wherein the amount of the poison compound is from about 1.0 to about 20 weight percent of the catalyst.

16. The method as recited in claim 6 wherein the step of operating the engine further comprises cycling the operating conditions at least once from low load and/or low speed to high load and/or high speed to result in the exhaust gas stream cycling from a temperature in the range of from 300° C. to 1200° C.

* * * * *